United States Patent
Stahl et al.

(10) Patent No.: US 11,773,074 B2
(45) Date of Patent: Oct. 3, 2023

(54) METHOD FOR AEROBIC OXIDATIVE COUPLING OF THIOPHENES WITH A LIGAND-SUPPORTED PALLADIUM CATALYST

(71) Applicant: Wisconsin Alumni Research Foundation, Madison, WI (US)

(72) Inventors: Shannon Stahl, Madison, WI (US); Stephen Tereniak, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

(21) Appl. No.: 17/087,926

(22) Filed: Nov. 3, 2020

(65) Prior Publication Data
US 2021/0047285 A1    Feb. 18, 2021

Related U.S. Application Data

(62) Division of application No. 16/243,394, filed on Jan. 9, 2019, now Pat. No. 10,858,334.

(Continued)

(51) Int. Cl.
C07D 333/22    (2006.01)
B01J 31/04     (2006.01)
(Continued)

(52) U.S. Cl.
CPC ............ *C07D 333/22* (2013.01); *B01J 31/04* (2013.01); *B01J 31/181* (2013.01); *B01J 31/183* (2013.01);
(Continued)

(58) Field of Classification Search
None
See application file for complete search history.

(56) References Cited

PUBLICATIONS

Farhangian, Hossein. Anticancer activity of novel amino acid derivative of palladium complex with phendione ligand against of human colon cancer cell line. J Biol Inorg Chem. (2017) 22:1055-1064.*

(Continued)

*Primary Examiner* — Samantha L Shterengarts
(74) *Attorney, Agent, or Firm* — QUARLES & BRADY LLP

(57) ABSTRACT

An oxidative homocoupling method of synthesizing certain 2,2'-bithiophenes from thiophenes using oxygen as the terminal oxidant is disclosed. In non-limiting examples, the method uses oxygen along with a catalytic system that includes palladium, an assistive ligand, and a non-palladium metal additive to catalyze one of the following reactions:

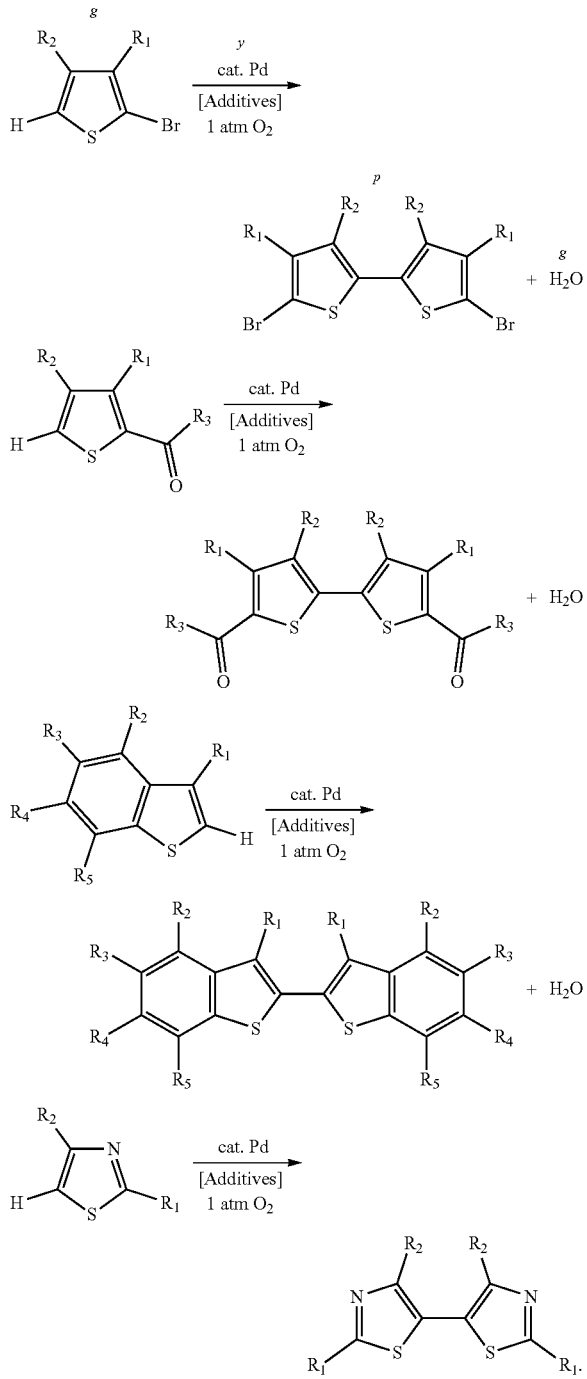

Associated catalytic systems and compositions are also disclosed.

17 Claims, 11 Drawing Sheets

Related U.S. Application Data

(60) Provisional application No. 62/615,248, filed on Jan. 9, 2018.

(51) Int. Cl.
 *C07D 277/32* (2006.01)
 *B01J 31/18* (2006.01)
 *C07D 333/54* (2006.01)
 *B01J 31/24* (2006.01)
 *B01J 31/22* (2006.01)

(52) U.S. Cl.
 CPC ......... *B01J 31/184* (2013.01); *B01J 31/1815* (2013.01); *B01J 31/1825* (2013.01); *B01J 31/2239* (2013.01); *B01J 31/2409* (2013.01); *C07D 277/32* (2013.01); *C07D 333/54* (2013.01); *B01J 2231/46* (2013.01); *B01J 2531/0205* (2013.01); *B01J 2531/16* (2013.01); *B01J 2531/824* (2013.01); *B01J 2531/842* (2013.01); *B01J 2540/10* (2013.01); *B01J 2540/22* (2013.01); *B01J 2540/225* (2013.01); *B01J 2540/40* (2013.01)

(56) References Cited

PUBLICATIONS

Shi Y. et al., "Oxygen as an oxidant in palladium/copper-cocatalyzed oxidative C—H/C—H cross-coupling between two heteroarenes," Science China Chemistry, 2015, vol. 58, No. 8, pp. 1292-1296, published May 4, 2015.
Hassan, J. et al., "A convenient catalytic route to symmetrical functionalized bithiophenes," Tetrahedron Letters, 1999, vol. 40, issue 5, Jan. 29, 1999.
Li N. et al., "Palladium-Catalyzed C—H Homocoupling of Furans and Thiophenes Using Oxygen as the Oxidant," Organic Letters, 2014, vol. 16, pp. 2732-2735, published May 7, 2014.
Masui K. et al., "Palladium-Catalyzed C—H Homocoupling of Thiophenes: Facile Construction of Bithiophene Structure," Journal of the American Chemical Society, 2004, vol. 126, pp. 5074-5075, published Mar. 1, 2004.
Shiotani, A. et al.,"Selective Coupling of Dimethyl Phthalate with Palladium Catalysts at Atmospheric Pressure," Journal of Molecular Catalysis, 1986, vol. 34,No. 1, pp. 57-66, published Jan. 1986.
Takahashi, M. et al.,"Palladium-Catalyzed C—H Homocoupling of Bromothiophene Derivatives and Synthetic Application to Well-Defined Oligothiophenes," Journal of the American Chemical Society, 2006, vol. 128, pp. 10930-10933, published Jul. 29, 2006.
Yuan Z. et al., "Palladium-Catalyzed Intramolecular Fluorooxylation of Styrenes," Chin. J. Chem., 2013, vol. 31, pp. 908-914, published Jul. 5, 2013.
Gary et al. ACS Catalysis, 2013, 3, 700-703.
Hull et al. J. Am. Chem. Soc., 2009, 131, 9651-9653.

* cited by examiner

G = Br, CHO, SnR$_3$

PBTTT-C14

PBTTPD

PffBT4T-2OD

8A:

8B:

8C:

8D:

8E:

METHOD FOR AEROBIC OXIDATIVE COUPLING OF THIOPHENES WITH A LIGAND-SUPPORTED PALLADIUM CATALYST

CROSS-REFERENCE TO RELATED APPLICATIONS

This application is a divisional of U.S. application Ser. No. 16/243,394 filed Jan. 9, 2019, which claims the benefit of U.S. provisional Application No. 62/615,248 filed Jan. 9, 2018. Each of these applications is incorporated by reference herein for all purposes.

STATEMENT REGARDING FEDERALLY SPONSORED RESEARCH/DEVELOPMENT

This invention was made with government support under GM119214 awarded by the National Institutes of Health and CHE1700982 awarded the National Science Foundation. The government has certain rights in the invention.

BACKGROUND OF THE INVENTION

Organic semiconductors have been widely investigated in applications including organic solar cells (OSCs),[1] organic field-effect transistors (OFETs),[2] organic light-emitting diodes (OLEDs),[3] and others with the goal of eventually replacing silicon-based semiconductor technology. The reason is that organic electronics have the potential to be lower in cost than silicon-based semiconductor technology due to cheaper materials processing and high-throughput device assembly.[2b]

Perhaps the most widely studied organic materials are those based on thiophenes.[4] Thiophenes have advantageous properties for their implementation in organic materials:[4a,5] (1) excellent charge transport properties, (2) high polarizability, (3) tunable optical and electrochemical properties, which is in part due to (4) predictable and reliable methods for their synthesis. Oligothiophenes specifically have been investigated for their material properties, as well as used as monomers for the synthesis of organic materials as a copolymer or cooligomer.

However, the synthesis of oligothiophenes and other materials based on thiophenes is dominated by numerous functional group installations and interconversions, which renders their synthesis time-consuming and inefficient.[6] Hence, more streamlined and efficient methods for the synthesis of thiophene materials are sought after.

A common building block for oligothiophenes and other thiophene-based materials is the 2,2'-bithiophene unit (FIG. 1). In order for the 2,2'-bithiophene unit to be connected to other organic monomers on both halves of the bithiophene, functional groups must be included, most commonly in the 5 and 5' positions. The most commonly used functional groups for this purpose are the (1) bromo functional group, (2) trialkylstannyl functional group, and (3) aldehyde functional group.

Several organic materials made from 5,5'-dibromo-4,4'-dialkyl-2,2'-bithiophenes are commercially available. One of these is the poly [2,5-bis(3-alkylthiophen-2-yl)thieno[3,2-b]thiophene] (PBTTT) series of polymers, which was developed and is licensed by Merck (FIG. 2A).[7] The original academic and patent papers utilized dodecyl groups; tetradecyl polymers are commercially available. Another commercially available thiophene-based polymer, PBTTPD (FIG. 2B),[8] is synthesized using 5,5'-bis(trimethylstannyl)-4,4'-didodecyl-2,2'-bithiophene, the latter of which can be prepared from 5,5'-dibromo-4,4'-didodecyl-2,2'-bithiophene (although it can also be prepared using the unbrominated compound 4,4'-didodecyl-2,2'-bithiophene) (see below for a discussion of how 5,5'-bis(trialkylstannyl)-2,2'-bithiophenes are prepared from 5,5'-dibromo-2,2'-bithiophenes). Other commercially available polymers, such as PffBT4T-20D (FIG. 2C),[9] are synthesized from a 5,5'-bis(trimethylstannyl)-2,2'-bithiophene building block.

Uses of 2,2'-Bithiophenes in Organic Materials Synthesis.

The 5,5'-dibromo-2,2'-bithiophene building block is used in a number of different reactions for the synthesis of longer building blocks or directly for the preparation of the final organic materials. These reactions include Pd-catalyzed reactions such as the Stille coupling and the Suzuki coupling (Scheme 1). 5,5'-dibromo-2,2'-bithiophenes can be modified in order to create unsymmetrical monomers, such as by the reduction of one of the two bromo groups to prepare a 5-bromo-2,2'-bithiophene. Many modifications are possible.

Scheme 1.
Reactions of 5,5'-dibromo-(4,4'-dialkyl-)2,2'-bithiophenes, including Stille-type couplings, for the synthesis of thiophene-containing materials.

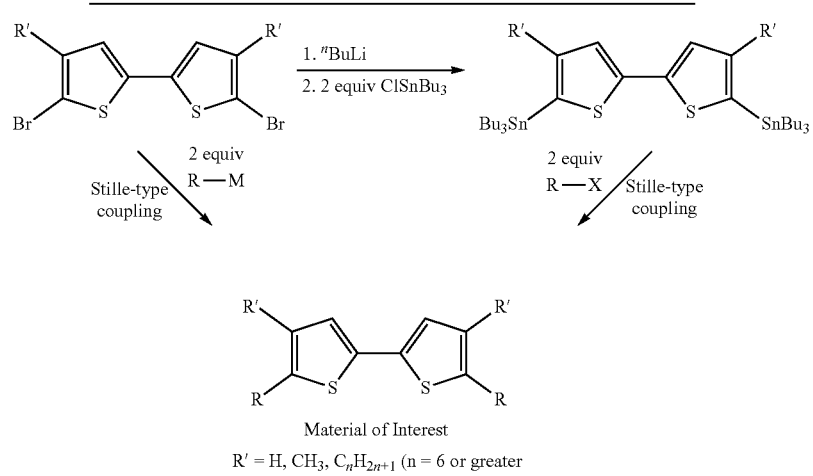

Material of Interest
R' = H, CH$_3$, C$_n$H$_{2n+1}$ (n = 6 or greater

The most common dibromobithiophene is 5,5'-dibromo-2,2'-bithiophene as it is the most readily accessible in this class. However, 5,5'-dibromo-2,2'-bithiophenes will, fairly frequently, be used with alkyl groups in the 4 and 4' positions. Occasionally, the alkyl group will be a methyl group (—CH$_3$), but most commonly (though not always), the alkyl group will be a straight (normal) chain with an even number of carbons ranging from 6 to 12. This means that the hexyl (C$_6$H$_{13}$), octyl (C$_8$H$_{17}$), decyl (C$_{10}$H$_{21}$), and dodecyl (C$_{12}$H$_{25}$) groups are used somewhat frequently. The reason is that alkyl groups that have six or more carbon atoms help provide solubility to the end-product organic materials in organic solvents. These, and other substitutions, on the thiophene core may also alter molecular packing within a crystal and the resulting opto-electronic properties.[2b]

The 5,5'-bis(carbaldehyde)-2,2'-bithiophene building block has been used in reactions ranging from phosphorus-based reactions such as the Horner-Wadsworth-Emmons (HWE) reaction[10] to imine condensations[11] and Knoevenagel condensations.[12] Other 2,2'-bithiophene derivatives synthesized in this work that have been investigated in organic materials synthesis applications include those based on 2,2'-bibenzo[b]thiophene,[13] 5,5'-bithiazole,[14] and 4,4',5,5'-tetrabromo-2,2'-bithiophene[15] (FIGS. 3A, 3B and 3C).

Synthetic Routes to 5,5'-Dibromo-2,2'-Bithiophenes.

The most commonly employed synthesis of 5,5'-dibromo-2,2'-bithiophene has two steps: (1) the reductive homocoupling of 2-bromothiophene to give 2,2'-bithiophene,[16] and (2) the dibromination of 2,2'-bithiophene to give 5,5'-dibromo-2,2'-bithiophene (Scheme 2).[17] The reductive homocoupling step is usually carried out with a nickel catalyst. This method generates a stoichiometric amount of magnesium salt waste. Other synthetic routes that have been used suffer from the same kind of drawbacks as those described below for 5,5'-dibromo-4,4'-dialkyl-2,2'-bithiophenes, such as the need for strong base and stoichiometric oxidants.[17a,18]

Scheme 2. Traditional synthetic route to 5,5'-dibromo-2,2'-bithiophene.

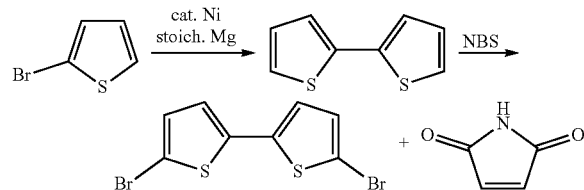

The main synthetic route described above for 5,5'-dibromo-2,2'-bithiophene is not used for the synthesis of 4,4'-dialkyl derivatives. This is probably because the requisite 2-bromo-4-alkylthiophene starting material is not readily available. If one were to monobrominate 3-alkylthiophene, it is not 2-bromo-4-alkylthiophene that is obtained but 2-bromo-3-alkylthiophene, in practically quantitative yield. For this reason, 2-bromo-3-alkylthiophenes are commercially available and useful starting materials for the synthesis of 5,5'-dibromo-4,4'-dialkyl-2,2'-bithiophenes.

There are several routes possible for the synthesis of 5,5'-dibromo-4,4'-dialkyl-2,2'-bithiophenes. Two methods are predominantly used. The first is an oxidative homocoupling route that uses a stoichiometric oxidant. In this route, 3-alkylthiophene is deprotonated with a strong base such as n-butyllithium or lithium diisopropylamide. Then, a stoichiometric oxidant is added such as copper(II) chloride or iron(III) acetate. Sometimes, the deprotonation step can be bypassed if iron(III) chloride is used as the oxidant. Finally, the 4,4'-dialkyl-2,2'-bithiophene intermediate is brominated, most commonly with N-bromosuccinimide (Scheme 3).[19] This route to 5,5'-dibromo-4,4'-dialkyl-2,2'-bithiophenes is not ideal because: (1) A stoichiometric metal salt byproduct must be removed in the purification of the final product, (2) stoichiometric salt waste is generated (unless iron(III) chloride is used), (3) an intermediate, 4,4'-dialkyl-2,2'-bithiophene, must be purified, (4) anhydrous solvents and an anaerobic atmosphere must be used so that the strong bases can work effectively, (5) very low temperatures (with a dry ice/acetone bath) are required for the reactions, and (6) the overall yields are only generally modest, and purification of the intermediate and final product can be time-consuming and tedious. Additionally, the regioselectivity of the oxidative coupling step can be problematic.[6]

Scheme 3.
Traditional synthetic route to 5,5'-dibromo-4,4'dialkyl-2,2'-bithiophene. Other stoichiometric oxidants such as iron(III) or quinone-based oxidants can be used instead of CuCl$_2$.

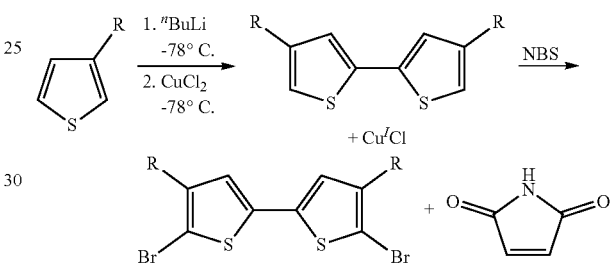

A second route for the synthesis of 5,5'-dibromo-4,4'-dialkyl-2,2'-bithiophenes is frequently used. This is an oxidative homocoupling route with 2-bromo-3-alkylthiophene as a starting material that uses a catalytic amount of a palladium(II) salt (Scheme 4).[20] The method requires the oxidant silver(I) fluoride in superstoichiometric quantities. The original report of this reaction used silver(I) fluoride directly.[21] However, due to its high cost, the authors of the original methodology sought to find a less expensive system and subsequently discovered that the silver(I) fluoride could be generated in situ using the cheaper reagents silver(I) nitrate and potassium fluoride.[22] In some ways, this method is an advancement over the oxidative homocoupling described previously in large part because only one step is needed from a readily commercially available starting material in order to obtain the desired 5,5'-dibromo-4,4'-dialkyl-2,2'-bithiophene product. (Note that there are some reports of the oxidative homocoupling of a 2-bromo-3-alkylthiophene using stoichiometric copper(II) choride,[23] but the reaction is still limited by the need for dry solvents, low temperatures, a stoichiometric oxidant, and an anaerobic atmosphere.) The palladium-catalyzed method that uses stoichiometric silver(I) suffers from a number of drawbacks: (1) stoichiometric silver waste must be removed in order to purify the desired product, (2) the reaction requires anhydrous solvent/conditions, (3) the reaction must be performed under an inert gas such as nitrogen, and (4) the reaction and/or the storage of the silver(I) salt must be excluded from light.

Scheme 4.
Pd-catalyzed oxidative homocoupling of 2-bromo(-3-alkyl)thiophene with superstoichiometric silver(I) fluoride to give 5,5'-dibromo-4,4'-dialkyl-2,2'-bithiophene.

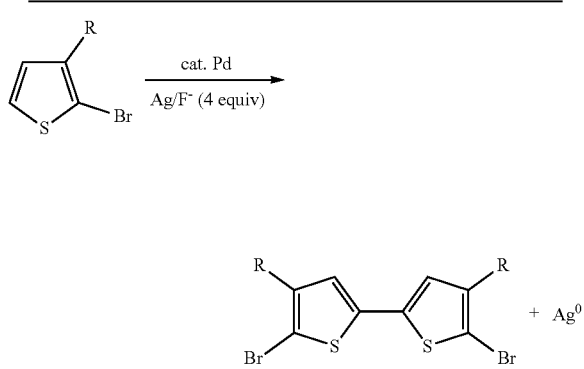

Scheme 5.
Targeted aerobic Pd-catalyzed oxidative homocoupling of 2-bromo(-3-alkyl)thiophene to give 5,5'-dibromo(-4,4'-dialkyl)-2,2'-bithiophene.

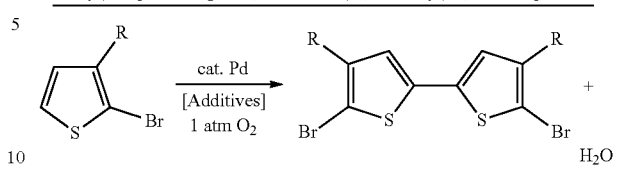

Synthetic Routes to Other 2,2'-Bithiophenes.

5,5'-dicarbaldehyde-2,2'-bithiophenes can be prepared in good yield by the lithiation of 5,5'-dibromo-2,2'-bithiophenes followed by exposure to DMF.[17a] Reductive homocoupling from 2-bromo-5-carbaldehyde using a palladium catalyst and a stoichiometric amine base has been shown.[23] 5,5'-bis(trialkylstannyl)-2,2'-bithiophenes can be prepared by lithiation of 5,5'-dibromo-2,2'-bithiophenes followed by addition of 2.0 equivalents of a trialkyltin chloride reagent.[25] The 5,5'-bis(trialkylstannyl)-4,4'-dialkyl-2,2'-bithiophenes have also been prepared by lithiation of 4,4'-dialkyl-2,2'-bithiophenes followed by addition of 2.0 equivalents of a trialkyltin chloride reagent.[26]

Development and Optimization of Aerobic Method for Homocoupling Bromothiophenes and Other Thiophenes.

The utility of 5,5'-dibromo-(4,4'-dialkyl-)2,2'-bithiophenes[19,27-28] and other functionalized bithiophene derivatives for the synthesis of organic materials strongly suggests that a more efficient oxidative homocoupling synthesis from 2-bromo(-3-alkyl)thiophenes and related compounds could be widely adopted by materials researchers. Ideally, this method would utilize oxygen as the terminal oxidant instead of stoichiometric metal salts such as silver(I), copper(II), or iron(III) (Scheme 4). An aerobic metal-catalyzed oxidative homocoupling of common thiophenes relevant to materials chemistry such as 2-bromo(-3-alkyl)thiophenes without stoichiometric additives has never been before reported in the literature.[29] Although there are dozens of literature-reported uses of a one-step synthesis of 5,5'-dibromo-4,4'-dialkyl-2,2'-bithiophenes from 2-bromo-3-alkylthiophenes with a palladium catalyst and stoichiometric silver(I) salts, there is a need in the art for new aerobic methods of bithiophene synthesis using a palladium catalyst.

SUMMARY OF THE INVENTION

We disclose herein methods of aerobic oxidative covalent homocoupling of certain thiophenes and thiophene analogs to the corresponding bithiophene or analog thereof using a ligand-supported Pd-containing catalytic system. Initially, the substrate 2-bromo-3-hexylthiophene was chosen for screening, as shown in Scheme 5, where R is a hexyl group.

Screening of known Pd-catalyzed aerobic arene homocoupling methods (all normalized to 10 mol % Pd loading at 110° C., with solvents chosen as appropriate so that they would not boil away during the reaction) gave yields that did not exceed 2%.[30] One of the methods was also chosen for solvent screening, but the best yield found upon screening different solvents was only 18%.[30d] Notably, a known Pd-catalyzed aerobic thiophene homocoupling methodology gave only trace yields of product.[30c] The substrates from this literature thiophene homocoupling report only contained alkyl groups, methoxy groups, and functional groups connected to the thiophene ring with a saturated alkylene linker. These results suggest that bromo-substituted thiophenes have different homocoupling requirements.

Optimization efforts began inspired by conditions developed by Ube Industries for the homocoupling of o-dimethylphthalate.[32] It was found that a mixture of a palladium cocatalyst, a copper cocatalyst, and a ligand could afford the desired 5,5'-dibromo-4,4'-dihexyl-2,2'-bithiophene product in yields better than the best found from the literature arene homocoupling methods. Yields of approximately 80% could be attained with a mixture of 3 mol % Pd(OAc)$_2$, 3 mol % Cu(OAc)$_2$·H$_2$O, and 3 mol % 1,10-phenanthroline-5,6-dione (phd) under one atmosphere O$_2$ at 120° C. in DMSO at 1.1 molar concentration for 16 hours. The optimal ligand, phd, is very unusual: it has never been used as an optimal ligand, to the best of our knowledge, in aerobic Pd oxidative catalysis.[34]

Further optimization efforts led to the discovery that the yield could be improved to 97% by adding 3 mol % benzoquinone to the catalytic mixture described in the previous paragraph. Additionally, other transition metal salts (e.g. Mn(OAc)$_2$·4H$_2$O) can be used instead of Cu(OAc)$_2$·H$_2$O, and use of alkaline earth metal salts instead of transition metal salts can provide moderate yields. As shown in the examples below, this work has also been extended to the aerobic covalent homocoupling of benzothiophenes, an acetal of thiophene-2-carbaldehyde, and 4-bromothiazole, among other functionalized thiophenes.

Accordingly, in a first aspect, the disclosure encompasses a method for synthesizing a 2,2'-bithiophene or analog thereof from two thiophenes or analogs thereof. The method includes contacting the two thiophenes or analogs thereof with oxygen gas and a catalyst comprising palladium. As a result of performing the method, the two thiophenes or analogs thereof are covalently coupled by aerobic oxidation to form the 2,2'-bithiophene or analog thereof.

In some embodiments, the two thiophenes or analogs thereof are not substituted exclusively with alkyl groups, alkoxy groups, alkanoate groups, wherein "alkanoate" refers to any ester with a saturated alkylene linker of at least one carbon atom in length separating the carbonyl group and the thiophene ring; alkanamide groups, wherein "alkanamide" refers to any amide with a saturated alkylene linker of at least one carbon atom in length separating the carbonyl group and the thiophene ring; alkoxyalkyl groups, wherein "alkoxyalkyl" refers to any alkyl-substituted ether with a saturated alkylene linker of at least one carbon atom in length separating the oxygen atom and the thiophene ring; and benzoxyalkyl groups, wherein "alkoxyalkyl" refers to any benzyl-substituted ether with a saturated alkylene linker of at least one carbon atom in length separating the oxygen atom and the thiophene ring.

In some embodiments, the method is not performed in the presence of a stoichiometric amount of silver salts.

In some embodiments, the two thiophenes or analogs thereof are the same compound.

In some embodiments, the 2,2'-bithiophene that is synthesized has the chemical structure:

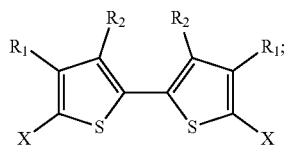

and the two thiophenes have the chemical structure:

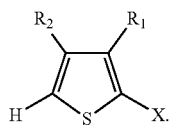

In some embodiments, X is a halogen, an alkyl, a trimethylsilyl (TMS), a thiophenyl, or a dioxolanyl. In certain non-limiting examples, X may be bromine, chlorine, n-hexyl, TMS,

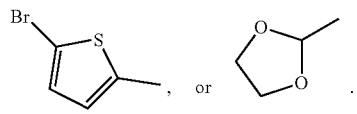

In some embodiments, $R_1$ and $R_2$ can be hydrogen, bromine, chlorine, fluorine, an alkoxycarbonyl group, an oxoalkyl group, or an alkyl group.

In some embodiments, the two thiophenes are 2-bromo-3-hexylthiophene or 2-chloro-3-hexylthiophene, and the corresponding 2,2'-bithiophene is 5,5'-dibromo-4,4'-dihexyl-2,2'-bithiophene (X is bromine, $R_1$ is n-hexyl, and $R_2$ is hydrogen) or 5,5'-dichloro-4,4'-dihexyl-2,2'-bithiophene (X is chlorine, $R_1$ is n-hexyl, and $R_2$ is hydrogen).

In some embodiments, the two thiophenes are 2-bromo-3-methylthiophene, and the 2,2'-bithiophene is 5,5'-dibromo-4,4'-dimethyl-2,2'-bithiophene (X is bromine, $R_1$ is methyl, and $R_2$ is hydrogen).

In some embodiments, the two thiophenes are 2-bromothiophene or 2-chlorothiophene, and the corresponding 2,2'-bithiophene is 5,5'-dibromo-2,2'-bithiophene (X is bromine, $R_1$ is hydrogen, and $R_2$ is hydrogen) or 5,5'-dichloro-2,2'-bithiophene (X is chlorine, $R_1$ is hydrogen, and $R_2$ is hydrogen).

In some embodiments, the two thiophenes are 2-bromo-3-dodecylthiophene, and the 2,2'-bithiophene is 5,5'-dibromo-4,4'-didocecyl-2,2'-bithiophene (X is bromine, $R_1$ is n-dodecyl, and $R_2$ is hydrogen).

In some embodiments, the two thiophenes are 2,3-dibromothiophene, 2,4-dibromothiophene, or 2-bromo-4-fluorothiophene; and the corresponding 2,2'-bithiophene is 4,4',5,5'-tetrabromo-2,2'-bithiophene (X is bromine, $R_1$ is bromine, and $R_2$ is hydrogen), 3,3',5,5'-tetrabromo-2,2'-bithiophene (X is bromine, $R_1$ is hydrogen, and $R_2$ is bromine) or 5,5'-dibromo-3,3'-difluoro-2,2'-bithiophene (X is bromine, $R_1$ is hydrogen, and $R_2$ is fluorine).

In some embodiments, the two thiophenes are:

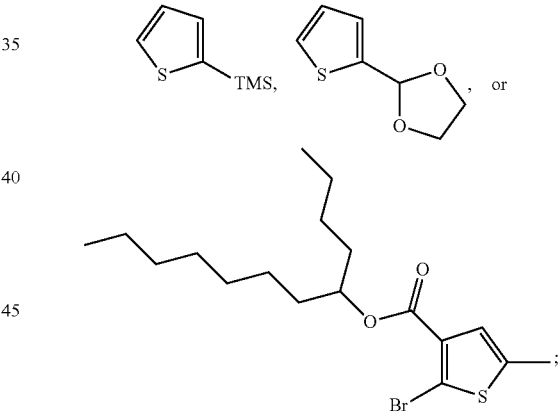

and the corresponding 2,2'-bithiophene is

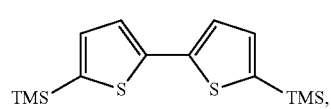

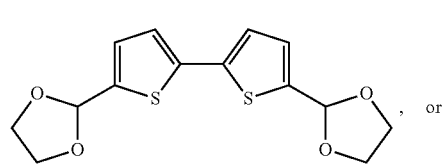

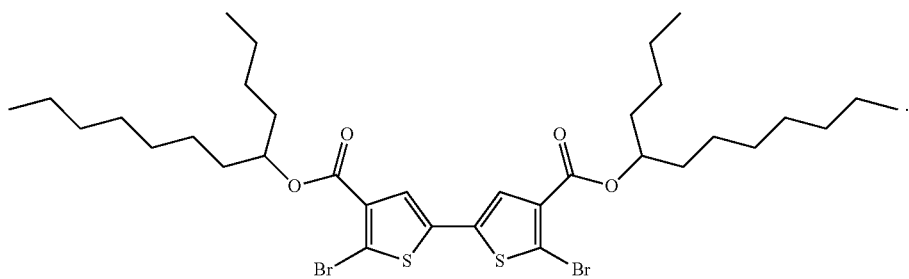

In some embodiments, the 2,2'-bithiophene that is synthesized is a 2,2'-bibenzo[b]thiophene, and the two thiophenes are benzo[b]thiophenes.

In some such embodiments, the 2,2'-bibenzo[b]thiophene has the chemical structure:

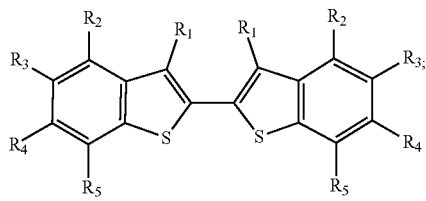

and
the two benzo[b]thiophenes have the chemical structure:

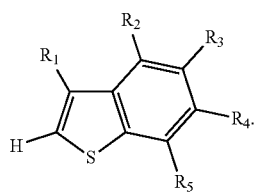

In some such embodiments, $R_1$, $R_2$, $R_3$, $R_4$ and $R_5$ are hydrogen or bromine.

In some such embodiments, the 2,2'-bibenzo[b]thiophene that is synthesized is 2,2'-bibenzo[b]thiophene, and the two benzo[b]thiophenes are unsubstituted benzo[b]thiophene ($R_1$, $R_2$, $R_3$, $R_4$ and $R_5$ are all hydrogen).

In other such embodiments, the 2,2'-bibenzo[b]thiophene that is synthesized is 3,3'-dibromo-2,2'-bibenzo[b]thiphene, and the two benzo[b]thiophenes are 3-bromobenzo[b]thiophene ($R_1$ is bromine; $R_2$, $R_3$, $R_4$ and $R_5$ are all hydrogen).

In some embodiments, the 2,2'-bithiophene that is synthesized is a 5,5'-bis(carbonyl)-2,2'-bithiophene, and the two thiophenes are 2-(1-oxoalkyl)thiophenes.

In some such embodiments, the 5,5'-bis-(1-oxoalkyl)-2,2'-bithiophene has the chemical structure:

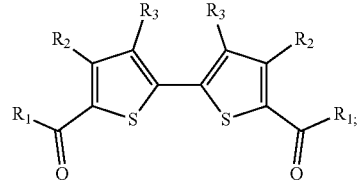

and
the two 2-(1-oxoalkyl)thiophenes have the chemical structure:

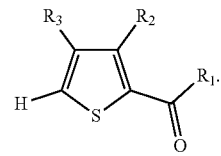

In some such embodiments, $R_1$ is an alkyl group, such as tert-butyl, or a hydrogen.

In some embodiments, $R_2$ and $R_3$ are hydrogen.

In some embodiments, the 5,5'-bis-(1-oxoalkyl)-2,2'-bithiophene that is synthesized is 5,5'-bis(carbaldehyde)-2,2'-bithiophene, and the two 2-(1-oxoalkyl)thiophenes are thiophene-2-carbaldehyde ($R_1$, $R_2$, and $R_3$ are all hydrogen).

In some embodiments, the 5,5'-bis-(1-oxoalkyl)-2,2'-bithiophene that is synthesized is 5,5'-bis(trimethylacetyl)-2,2'-bithiophene, and the two 2-(1-oxoalkyl)thiophenes are 2-trimethylacetylthiophene ($R_1$ is tert-butyl; $R_2$ and $R_3$ are hydrogen).

In some embodiments, the 2,2'-bithiophene analog that is synthesized is a 5,5'-bithiazole, and the two thiophene analogs are thiazoles.

In some such embodiments, the 5,5'-bithiazole has the chemical structure:

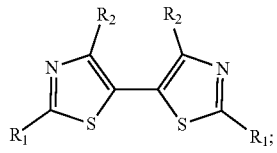

and
the two thiazoles have the chemical structure:

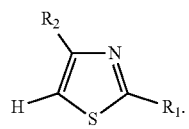

In some such embodiments, $R_1$ is hydrogen.

In some such embodiments, $R_2$ is bromine.

In some embodiments, the 5,5'-bithiazole that is synthesized is 4,4'-dibromo-5,5'-bithiazole, and the two thiazoles are 4-bromothiazole ($R_1$ is hydrogen, $R_2$ is bromine).

In some embodiments, the palladium is in the form of dipalladium(0) tris(dibenzylideneacetylacetone). In other embodiments, the palladium is in the form of a palladium salt. In some such embodiments, the palladium salt is palladium(II) acetate, palladium(II) propionate, palladium(II) pivalate, palladium(II) benzoate, palladium(II) acetylacetonate, palladium(II) trifluoroacetate, palladium(II) nitrate dihydrate, or palladium(II) iodide.

In some embodiments, the catalyst further includes a ligand. In some such embodiments, the ligand is a 1,10-phenanthroline; a 2,2'-bipyridine, a 2,2'-bipyrimidine; a 4,5-diazafluoren-9-one; a quinoline; a 1,10-phenanthroline; a bis(arylimino)acenaphthene; or a 2,2'-biquinoline.

In some embodiments, the ligand is a 1,10-phenanthroline having the chemical formula:

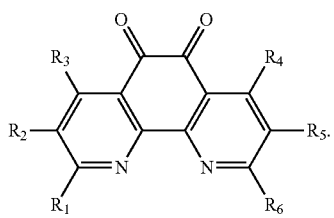

In some such embodiments, 1, 2, 3, 4, 5 or all 6 of $R_1$, $R_2$, $R_3$, $R_4$, $R_5$ and $R_6$ are hydrogen. In some such embodiments, all 6 of $R_1$, $R_2$, $R_3$, $R_4$, $R_5$ and $R_6$ are hydrogen (the ligand is 1,10-phenanthroline-5,6-dione (phd)).

In some embodiments, the ligand is a pyridine having the chemical formula:

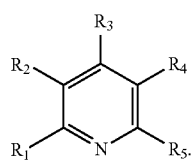

In some such embodiments, one or more of $R_1$, $R_2$, $R_3$, $R_4$, and $R_5$ are fluorine, chlorine, bromine, tert-butyl, methoxy, dimethylamino, hydrogen, methyl, acetyl, nitro, or hydroxyl.

In some embodiments, the ligand is a 2,2'-bipyridine having the chemical formula:

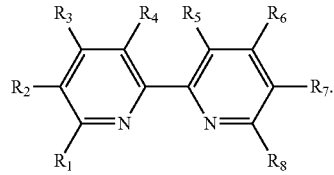

In some such embodiments, one or more of $R_1$, $R_2$, $R_3$, $R_4$, $R_5$, $R_6$, $R_7$ and $R_8$ are hydrogen, tert-butyl, methoxy, methyl, phenyl, or trifluoromethyl.

In some embodiments, the ligand is a 2,2'-bipyrimidine having the chemical formula:

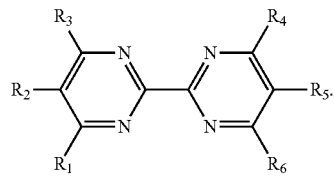

In some such embodiments, one or more of $R_1$, $R_2$, $R_3$, $R_4$, $R_5$, and $R_6$ is hydrogen.

In some embodiments, the ligand is a 4,5-diazafluoren-9-one having the chemical formula:

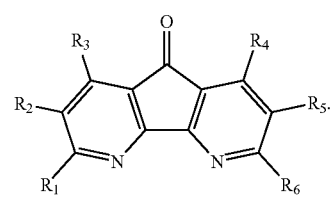

In some such embodiments, one or more of $R_1$, $R_2$, $R_3$, $R_4$, $R_5$, and $R_6$ is hydrogen.

In some embodiments, the ligand is a quinoline having the chemical formula:

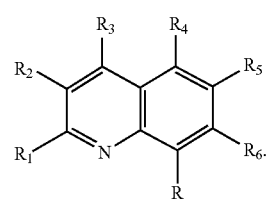

In some such embodiments, one or more of $R_1$, $R_2$, $R_3$, $R_4$, $R_5$, $R_6$ and $R_7$ is hydrogen.

In some embodiments, the ligand is a 1,10-phenanthroline having the chemical formula:

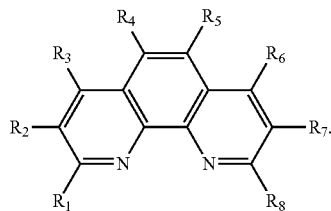

In some such embodiments, one or more of $R_1$, $R_2$, $R_3$, $R_4$, $R_5$, $R_6$ $R_7$, and $R_8$ is hydrogen, methyl, or phenyl.

In some embodiments, the ligand is a bis(arylimino) acenaphthene having the chemical formula:

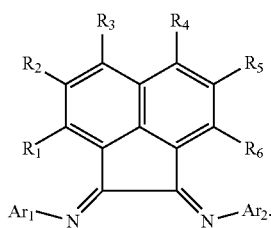

In some such embodiments, one or more of $R_1$, $R_2$, $R_3$, $R_4$, $R_5$, and $R_6$ is hydrogen. In some such embodiments, one or both of $Ar_1$ and $Ar_2$ are 4-methylphenyl or 1,3,5-trimethylphenyl.

In some embodiments, the ligand is a 2,2'-biquinoline having the chemical formula:

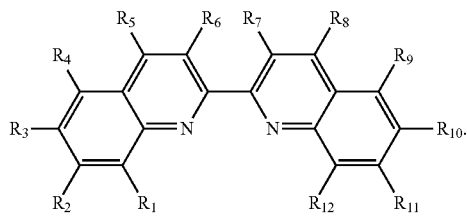

In some such embodiments, one or more of $R_1$, $R_2$, $R_3$, $R_4$, $R_5$, $R_6$, $R_7$, $R_8$, $R_9$, $R_{10}$, $R_{11}$ and $R_{12}$ is hydrogen.

In some embodiments, the ligand is present in catalytic amounts, not in stoichiometric amounts.

In some embodiments, the catalyst further includes a transition metal. In some such embodiments, the transition metal is zinc, copper, manganese, nickel, iron, cobalt, or silver. In some such embodiments, the transition metal is in the form of metallic copper. In some such embodiments, the transition metal is in the form of a transition metal salt, such as zinc(II) acetate, copper(II) acetate monohydrate, iron(II) acetate, cobalt(II) acetate, manganese(II) acetate tetrahydrate, nickel(II) acetate tetrahydrate, or silver(I) acetate.

In some embodiments, the catalyst further includes a redox-active organic mediator.

In some such embodiments, the redox-active organic mediator is a substituted or unsubstituted benzoquinone, or a substituted or unsubstituted hydroquinone.

In some embodiments, the method is performed in the absence of silver salts.

In some embodiments, the method is not performed under highly acidic or highly basic conditions.

In some embodiments, the method is performed at a temperature of more than 100° C. or more than 60° C.

In a second aspect, the disclosure encompasses a catalytic system for catalyzing the synthesis of a 2,2'-bithiophene or analog thereof from two thiophenes or analogs thereof. The system includes oxygen gas; palladium; a transition metal, alkali metal, alkaline earth metal, bismuth salt, or aluminum salt (non-limiting examples include cesium, magnesium, calcium, strontium or bismuth); and a ligand. Each of these components may optionally have one or more of the limitations described above.

In some embodiments, the system further includes a redox-active organic mediator.

In some such embodiments, the redox-active organic mediator is a substituted or unsubstituted benzoquinone, or a substituted or unsubstituted hydroquinone.

In some embodiments, the system does not include a stoichiometric amount of silver.

In some embodiments, the system is not highly acidic or highly basic.

In a third aspect, the disclosure encompasses a compound having the chemical structure:

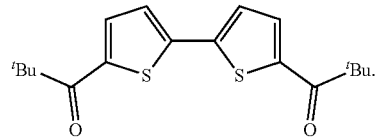 [SMILES: CC(C)(C)C(=O)c1ccc(-c2ccc(C(=O)C(C)(C)C)s2)s1]

The following descriptions are of certain exemplary embodiments, and should not be considered limiting. The full scope of the invention is defined by the appended claims.

BRIEF DESCRIPTION OF THE DRAWINGS

FIG. 2A) PBTTT-C14 polymer; FIG. 2B) PBTTPD polymer; FIG. 2C) PffBT4T-2OD polymer.

FIG. 3A) 2,2'-bibenzothiophene; FIG. 3B) 5,5'-bithiazole; FIG. 3C) 4,4',5,5'-tetrabromo-2,2'-bithiophene.

DETAILED DESCRIPTION

I. In General

Figure 1:
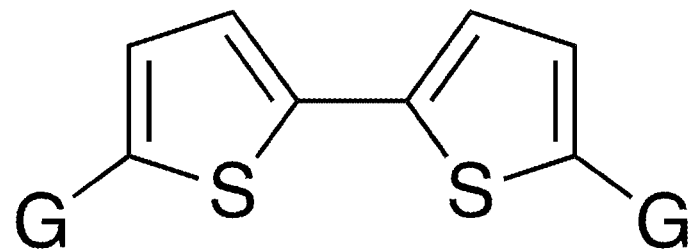
FIG. 1 shows the chemical structure of the 2,2'-bithiophene monomer with common substituents in the 5 and 5' positions: bromo, carbaldehyde, or trialkylstannyl.
Figure 2A:
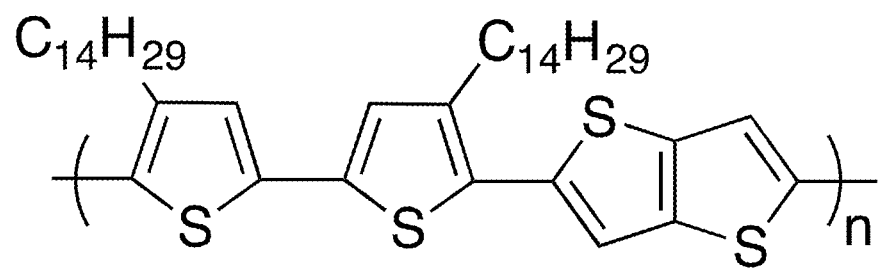
FIGS. 2A, 2B and 2C show the chemical structures of commercialized thiophene-based organic polymers containing the 2,2'-bithiophene monomer.
Figure 2B:
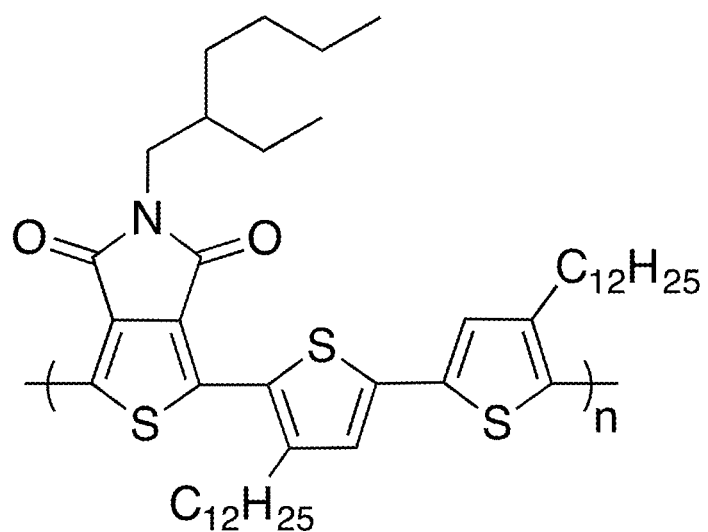
Figure 2C:
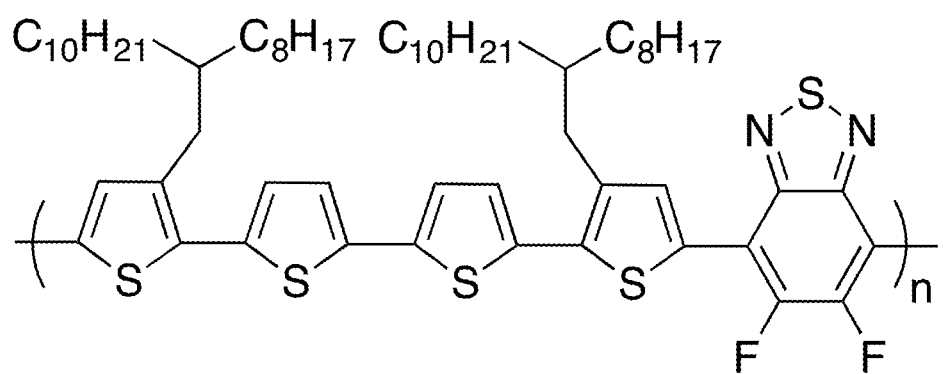
Figure 3A:
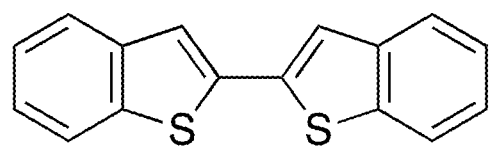
FIGS. 3A, 3B and 3C show the chemical structures of the cores of other biheteroaryls whose syntheses were investigated in this work.
Figure 3B:
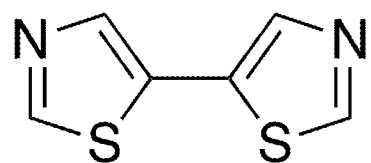
Figure 3C:
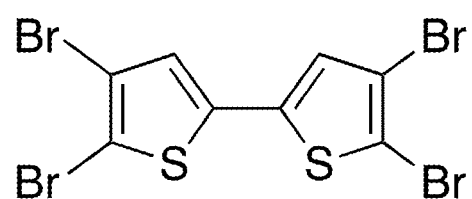
Figure 4:
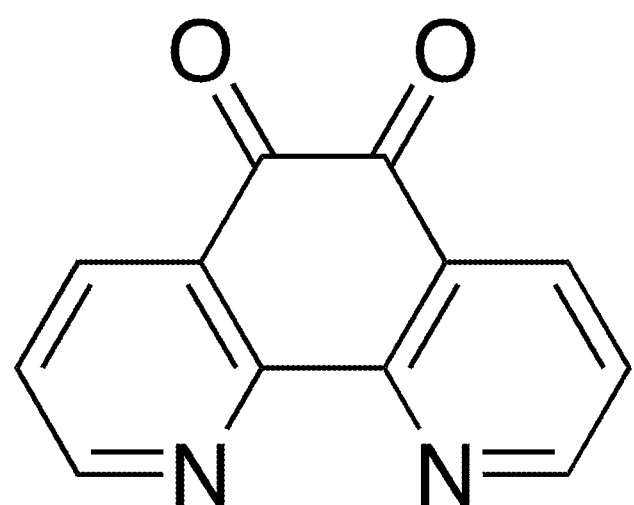
FIG. 4 shows the chemical structure of the optimal ancillary ligand in this work: 1,10-phenanthroline-5,6-dione (phd).

This disclosure is not limited to the particular methodology, protocols, materials, and reagents described, as these may vary. Furthermore, the terminology used herein is for the purpose of describing particular embodiments only, and is not intended to limit the scope of the present invention which will be limited only by the pending claims.

As used herein and in the appended claims, the singular forms "a", "an", and "the" include plural reference unless the context clearly dictates otherwise. As well, the terms "a" (or "an"), "one or more" and "at least one" can be used interchangeably herein. The terms "comprising", "including", and "having" can be used interchangeably.

Unless defined otherwise, all technical and scientific terms used herein have the same meanings as commonly understood by one of ordinary skill in the art. Although any methods and materials similar or equivalent to those described herein can be used in the practice or testing of the present invention, the methods and materials of several embodiments will now be described. All publications and patents specifically mentioned herein are incorporated by reference in their entirety for all purposes.

II. The Invention

We disclose herein a new method for the aerobic oxidative covalent homocoupling of certain thiophenes and thiophene analogs to the corresponding 2,2'-bithiophenes or analogs thereof. The method uses oxygen as the terminal oxidant, and also uses a catalyst that includes palladium, catalytic amounts of an additional metal additive, such as copper(II) acetate monohydrate, and an assistive ligand, such as 1,10-phenanthroline-5,6-dione (phd). A redox-active organic mediator, such as benzoquinone (BQ), can also be included in the method to optimize the results.

The bithiophene products are useful monomeric intermediates for material synthesis, through reactions such as Stille couplings, stannylations, Suzuki couplings, and others. The resulting oligothiophene moieties are used to enhance conductivity, increase material solubility, and act as a spacer within a material. As a result, these materials have a number of potential uses in existing and emerging areas.

The disclosed methods provide a number of advantages over existing techniques. When compared to Pd-catalyzed oxidative reactions that utilize stoichiometric silver (I) salts, the aerobic conditions disclosed herein are environmentally friendly in that they do not result in stoichiometric amounts of toxic byproducts. Other methods, while catalyst-free, require stoichiometric addition of a strong base (e.g., n-butyllithium) that is extremely flammable and moisture sensitive followed by the addition of a stoichiometric oxidant (e.g., copper(II) salt, an iron(III) salt, or a quinone) and generate stoichiometric byproducts. In contrast, this disclosure provides a one-step catalytic method for producing high yields of a desirable product while minimizing unwanted byproducts.

As non-limiting examples, the method may be used to catalyze the following reactions:

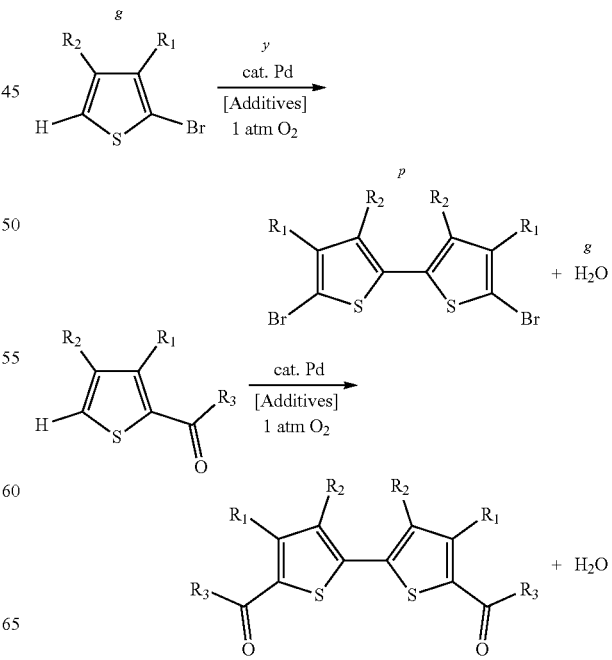

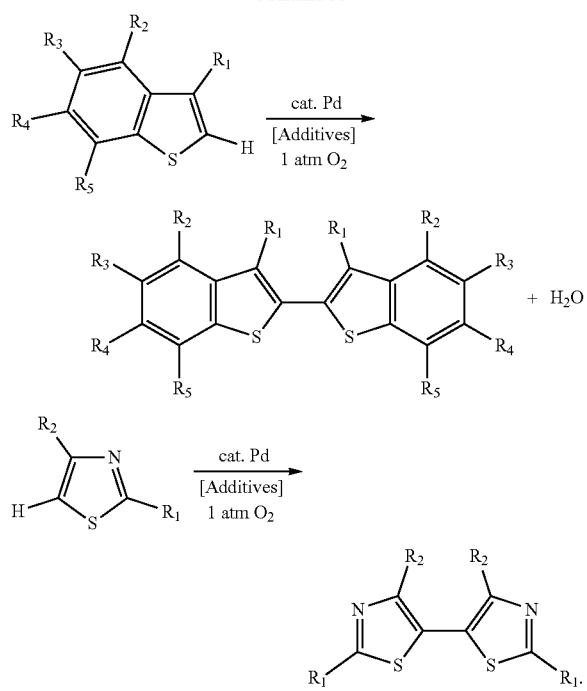
More specific non-limiting examples include the following:
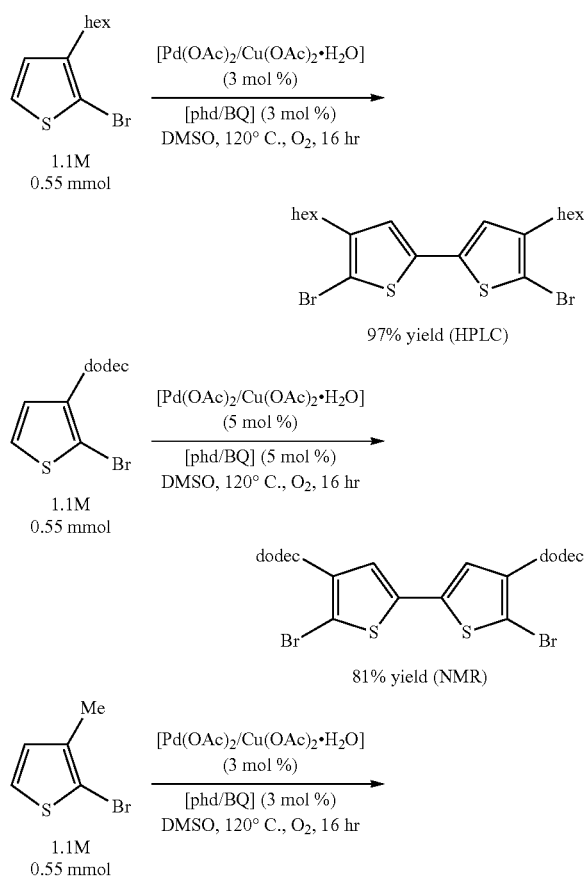
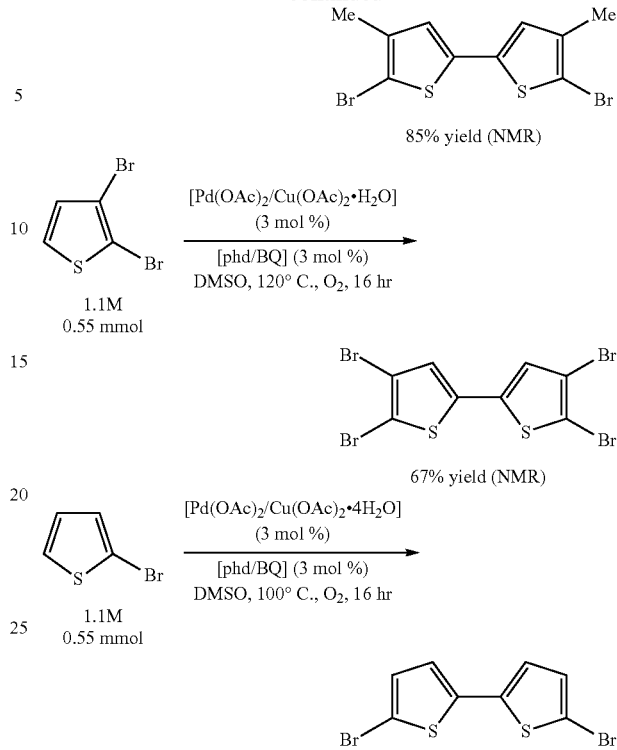

19
-continued

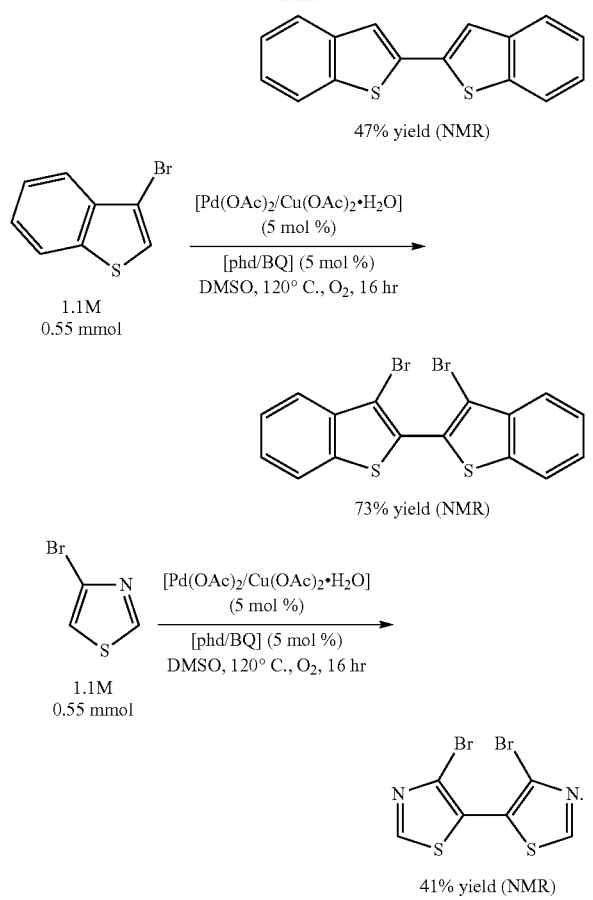

Furthermore, this disclosure is the first reported use of 1,10-phenanthroline-5,6-dione (phd) as an effective ligand in aerobic Pd catalysis:

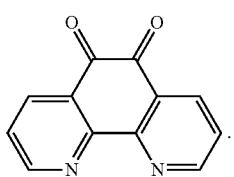 [SMILES: O=C1C(=O)c2cccnc2-c2ncccc21]

In addition, this disclosure is the first reported synthesis of the following 2,2'-bithiophene:

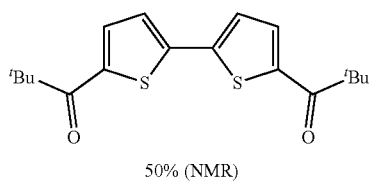 [SMILES: CC(C)(C)C(=O)c1ccc(-c2ccc(C(=O)C(C)(C)C)s2)s1]

50% (NMR)

Further details regarding specific embodiments and syntheses thereof are provided in the following examples. These specific embodiments do not in any way limit the scope of the disclosure.

20
III. Examples

Example 1 (Scheme 5): Aerobic Pd-Catalyzed Oxidative Homocoupling of 2-Bromo-3-Hexylthiophene to Give 5,5'-Dibromo-4,4'-Dihexyl-2,2'-Bithiophene To a 13×100 mm borosilicate glass heavy wall test tube was added benzoquinone (BQ) (1.8 mg, 0.017 mmol) and $Cu(OAc)_2 \cdot H_2O$ (3.3 mg, 0.017 mmol). A stock solution of $Pd(OAc)_2$ (95.9 mg, 0.427 mmol, 85.4 mM) in 5.0 mL DMSO was created. A stock solution of 1,10-phenanthroline-5,6-dione (phd) (89.7 mg, 0.427 mmol, 85.4 mM) in 5.0 mL DMSO was created. To the test tube was added 195 μL (0.017 mmol) of each of the stock solutions. Then, 2-bromo-3-hexylthiophene (112.5 μL, 0.555 mmol) was added to the test tube. The test tube with reaction mixture was placed on an orbital mixing block with heating element. The mixing block was sealed, purged with $O_2$ for five minutes, cooling water was turned on, and then the block was heated to 120° C. under 1 atm $O_2$ with shaking for 16 hours.

After 16 hours, the shaking was stopped, the block was depressurized, and the reaction test tube was removed and allowed to cool. An aliquot of a stock solution of phenanthrene in THF was added to the reaction mixture, and the DMSO/THF mixture was filtered through Celite. The test tube was washed with more THF, which was filtered through the Celite, and then the Celite was washed once more with THF. The filtrate was diluted with additional THF, and then it was shaken so that everything was evenly mixed.

The reaction mixture was assayed by high pressure liquid chromatography (HPLC) against a calibration curve of 5,5'-dibromo-4,4'-dihexyl-2,2'-bithiophene (commercially available from TCI America) and phenanthrene using a reverse phase column (elutent: 100% acetonitrile, 2 mL/minute). The HPLC yield of 5,5'-dibromo-4,4'-dihexyl-2,2'-bithiophene was determined to be 97%.

This crude product displayed one singlet in the $^1H$ NMR spectrum in the aromatic region, consistent with the assigned product. Furthermore, a number of different crude product mixtures from different crude reactions were combined and purified on reverse phase column chromatography, and the combined chromatography fractions which had the same HPLC retention time as 5,5'-dibromo-4,4'-dihexyl-2,2'-bithiophene possessed a $^1H$ NMR spectrum which matched that of 5,5'-dibromo-4,4'-dihexyl-2,2'-bithiophene.

Example 2 (Scheme 6): Aerobic Pd-Catalyzed Oxidative Homocoupling of 2-Bromo-3-Methylthiophene to Give 5,5'-Dibromo-4,4'-Dimethyl-2,2'-Bithiophene

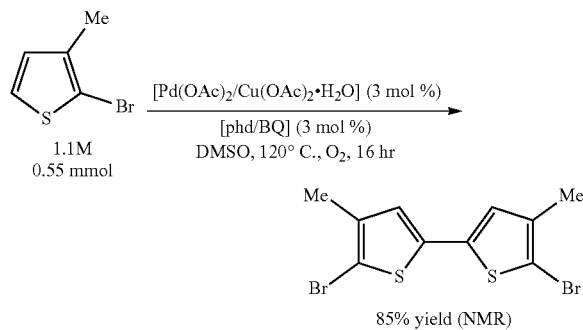

To a 13×100 mm borosilicate glass heavy wall test tube was added 2-bromo-3-methylthiophene (97.4 mg, 0.55 mmol). A stock solution of Pd(OAc)$_2$ (84.2 mg, 0.375 mmol, 75.0 mM) and BQ (40.5 mg, 0.375 mmol, 75.0 mM) in 5.0 mL DMSO was created. A stock solution of Cu(OAc)$_2$·H$_2$O (57.1 mg, 0.286 mmol, 143 mM) and phd (60.1 mg, 0.286 mmol, 143 mM) in 2.0 mL DMSO was created. Then, 62 µL DMSO, followed by 220 µL (0.0165 mmol) of the Pd(OAc)$_2$/BQ stock solution, and 115 µL (0.0164 mmol) of Cu(OAc)$_2$·H$_2$O/phd stock solution were added to the test tube. The test tube with reaction mixture was placed on an orbital mixing block with heating element. The mixing block was sealed, purged with O$_2$ for five minutes, cooling water was turned on, and then the block was heated to 120° C. under 1 atm O$_2$ with shaking for 16 hours. After 16 hours, the shaking was stopped, the block was depressurized, and the reaction test tube was removed and allowed to cool.

An aliquot of a stock solution of dibromomethane in THF was added to the reaction mixture, and the DMSO/THF mixture was filtered through the Celite, and then the Celite was washed once more with THF. The filtrate was diluted with additional THF, and then it was shaken so that everything was evenly mixed. The reaction mixture was assayed by $^1$H NMR spectroscopy against the dibromomethane standard. The $^1$H NMR yield of 5,5'-dibromo-4,4'-dimethyl-2,2'-bithiophene was determined to be 85%.

Example 3 (Scheme 7): Aerobic Pd-Catalyzed Oxidative Homocoupling of 2-(Trimethylacetyl)thiophene to Give 5,5'-Bis(trimethylacetyl)-2,2'-Bithiophene

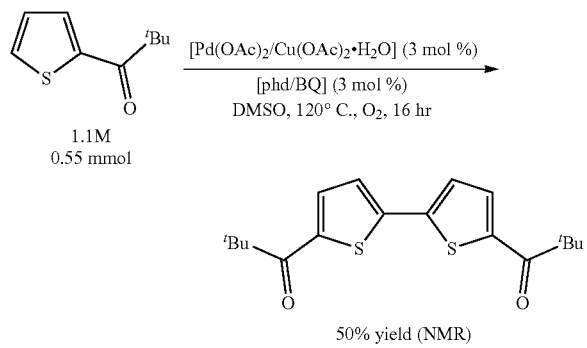

The same procedure as Example 2 was used, except that 2-(trimethylacetyl)thiophene (92.5 mg, 0.55 mmol) was used instead of 2-bromo-3-methylthiophene. The $^1$H NMR yield of 5,5'-bis(trimethylacetyl)-2,2'-bithiophene was determined to be 50%.

Example 4 (Scheme 8): Aerobic Pd-Catalyzed Oxidative Homocoupling of Benzothiophene to Give 2,2'-Bibenzothiophene To a 13×100 mm borosilicate glass heavy wall test tube was added benzothiophene (73.8 mg, 0.55 mmol). A stock solution of Pd(OAc)$_2$ (16.8 mg, 0.075 mmol, 75 mM) and BQ (8.1 mg, 0.075 mmol, 75 mM) in 1.0 mL DMSO was created. A stock solution of Cu(OAc)$_2$·H$_2$O (57.1 mg, 0.286 mmol, 143 mM) and phd (60.1 mg, 0.286 mmol, 143 mM) in 2.0 mL DMSO was created. Then, 100 µL DMSO, followed by 220 µL (0.0165 mmol) of the Pd(OAc)$_2$/BQ stock solution, and 115 µL (0.0164 mmol) of the Cu(OAc)$_2$·H$_2$O/phd stock solution were added to the test tube. The test tube with reaction mixture was placed on an orbital mixing block with heating element. The mixing block was sealed, purged with O$_2$ for five minutes, cooling water was turned on, and then the block was heated to 120° C. under 1 atm O$_2$ with shaking for 48 hours.

After 48 hours, the shaking was stopped, the block was depressurized, and the reaction test tube was removed and allowed to cool. An aliquot of a stock solution of 1,3,5-trimethoxybenzene in THF was added to the reaction mixture, and the DMSO/THF mixture was filtered through the Celite, and then the Celite was washed once more with THF. The filtrate was diluted with additional THF, and then it was shaken so that everything was evenly mixed.

The reaction mixture was assayed by $^1$H NMR spectroscopy against the 1,3,5-trimethoxybenzene standard. The $^1$H NMR yield of 2,2'-bibenzothiophene was determined to be 47%.

Example 5 (Scheme 9): Aerobic Pd-Catalyzed Oxidative Homocoupling of 2-Thiophenecarbaldehyde to Give 5,5'-Bis(carbaldehyde)-2,2'-Bithiophene

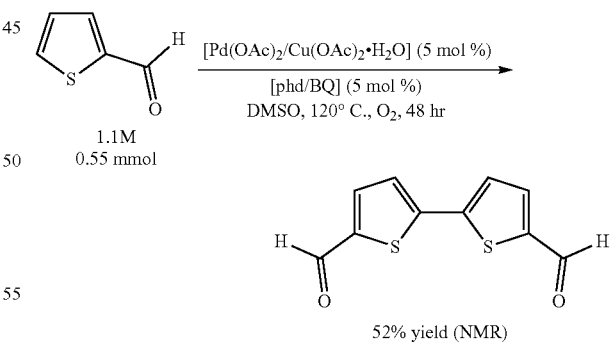

To a 13×100 mm borosilicate glass heavy wall test tube was added thiophenecarbaldehyde (61.7 mg, 0.55 mmol). To this test tube were added Pd(OAc)$_2$ (6.2 mg, 0.028 mmol), Cu(OAc)$_2$·H$_2$O (5.5 mg, 0.028 mmol), phd (5.8 mg, 0.028 mmol), and BQ (3.0 mg, 0.028 mmol). Then, 450 µL DMSO was added to the test tube. The test tube with reaction mixture was placed on an orbital mixing block with heating element. The mixing block was sealed, purged with O$_2$ for five minutes, cooling water was turned on, and then the block was heated to 120° C. under 1 atm $O_2$ with shaking for 48 hours. After 48 hours, the shaking was stopped, the block was depressurized, and the reaction test tube was removed and allowed to cool.

An aliquot of a stock solution of 1,3,5-trimethoxybenzene in THF was added to the reaction mixture, and the DMSO/THF mixture was filtered through the Celite, and then the Celite was washed once more with THF. The filtrate was diluted with additional THF, and then it was shaken so that everything was evenly mixed.

The reaction mixture was assayed by $^1H$ NMR spectroscopy against the 1,3,5-trimethoxybenzene standard. The $^1H$ NMR yield of 5,5'-bis(carbaldehyde)-2,2'-bithiophene was determined to be 52%.

Example 6 (Scheme 10): Aerobic Pd-Catalyzed Oxidative Homocoupling of 2-Bromothiophene to Give 5,5'-Dibromo-2,2'-Bithiophene

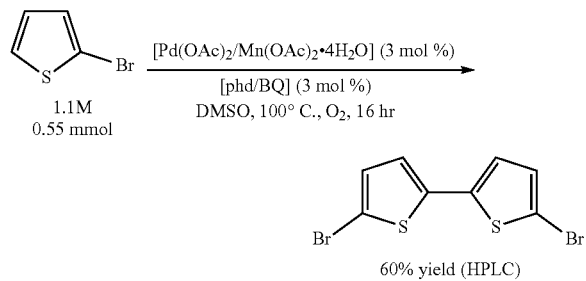

60% yield (HPLC)

To a 13×100 mm borosilicate glass heavy wall test tube was added phd (3.5 mg, 0.017 mmol) and $Mn(OAc)_2 \cdot 4H_2O$ (4.0 mg, 0.017 mmol). A stock solution of $Pd(OAc)_2$ (148 mg, 0.660 mmol, 66.0 mM) in 10.0 mL DMSO was created. A stock solution of BQ (44.6 mg, 0.413 mmol, 82.6 mM) in 5.0 mL DMSO was created. To the test tube was added 250 μL (0.017 mmol) of the $Pd(OAc)_2$ stock solution and 200 μL (0.017 mmol) of the BQ stock solution. Then, 2-bromothiophene (53 μL, 0.55 mmol) was added to the test tube. The test tube with reaction mixture was placed on an orbital mixing block with heating element. The mixing block was sealed, purged with $O_2$ for five minutes, cooling water was turned on, and then the block was heated to 100° C. under 1 atm $O_2$ with shaking for 16 hours. After 16 hours, the shaking was stopped, the block was depressurized, and the reaction test tube was removed and allowed to cool.

An aliquot of a stock solution of phenanthrene in THF was added to the reaction mixture, and the DMSO/THF mixture was filtered through Celite. The test tube was washed with more THF, which was filtered through the Celite, and then the Celite was washed once more with THF. The filtrate was diluted with additional THF, and then it was shaken so that everything was evenly mixed.

The reaction mixture was assayed by HPLC against a calibration curve of 5,5'-dibromo-2,2'-bithiophene and phenanthrene using a reverse phase column (elutent: 100% acetonitrile, 2 mL/minute). The HPLC yield of 5,5'-dibromo-2,2'-bithiophene was determined to be 60%.

Example 7 (Scheme 11): Aerobic Pd-catalyzed Oxidative Homocoupling of 4-bromothiazole to give 4,4'-dibromo-2,2'-bithiazole

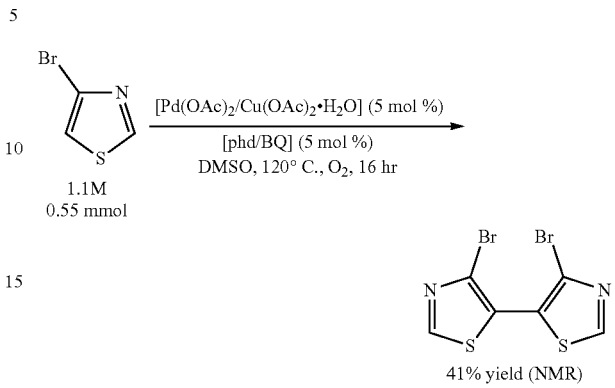

41% yield (NMR)

To a 13×100 mm borosilicate glass heavy wall test tube was added 4-bromothiazole (90.2 mg, 0.55 mmol). $Pd(OAc)_2$ (6.2 mg, 0.028 mmol) was added to the test tube. A stock solution of $Cu(OAc)_2 \cdot H_2O$ (32.8 mg, 0.164 mmol, 82.1 mM), phd (34.5 mg, 0.164 mmol, 82.1 mM), and BQ (17.7 mg, 0.164 mmol, 82.1 mM) in 2.0 mL DMSO was created. Then, 335 μL (0.028 mmol) of the stock solution was added to the test tube. Finally, 115 μL DMSO was added to the test tube. The test tube with reaction mixture was placed on an orbital mixing block with heating element. The mixing block was sealed, purged with $O_2$ for five minutes, cooling water was turned on, and then the block was heated to 120° C. under 1 atm $O_2$ with shaking for 16 hours. After 16 hours, the shaking was stopped, the block was depressurized, and the reaction test tube was removed and allowed to cool.

An aliquot of a stock solution of 1,3,5-trimethoxybenzene in THF was added to the reaction mixture, and the DMSO/THF mixture was filtered through the Celite, and then the Celite was washed once more with THF. The filtrate was diluted with additional THF, and then it was shaken so that everything was evenly mixed.

The reaction mixture was assayed by $^1H$ NMR spectroscopy against the 1,3,5-trimethoxybenzene standard. The $^1H$ NMR yield of 4,4'-dibromo-2,2'-bithiazole was determined to be 41%.

Example 8 (Scheme 12): Aerobic Pd-Catalyzed Oxidative Homocoupling of 2-Bromo-3-Dodecylthiophene to Give 5,5'-Dibromo-4,4'-Didodecyl-2,2'-Bithiophene

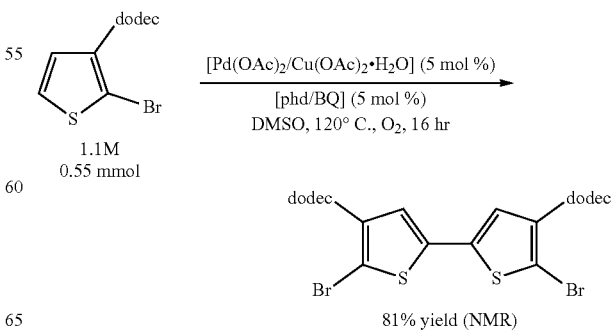

81% yield (NMR)

The same procedure as Example 7 was used, except that 2-bromo-3-dodecylthiophene (182 mg, 0.55 mmol) was used instead of 4-bromothiazole, and 92.5 µL DMSO was added. The $^1$H NMR yield of 5,5'-dibromo-4,4'-didodecyl-2,2'-bithiophene was determined to be 81%.

Example 9 (Scheme 13): Aerobic Pd-Catalyzed Oxidative Homocoupling of 3-Bromobenzothiophene to Give 3,3'-Dibromo-2,2'-Bibenzothiophene

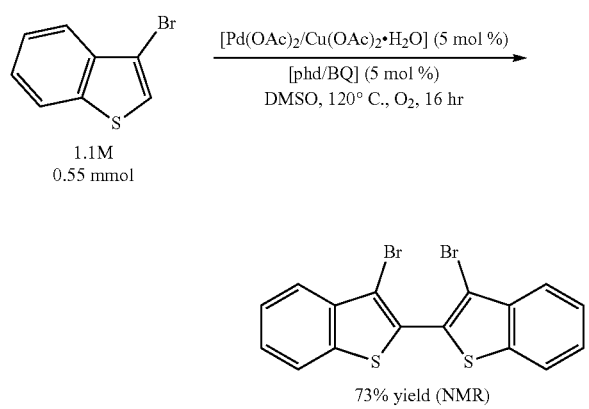

73% yield (NMR)

The same procedure as Example 7 was used, except that 3-bromobenzothiophene (117 mg, 0.55 mmol) was used instead of 4-bromothiazole, and 92.5 µL additional DMSO was added. The $^1$H NMR yield of 3,3'-dibromo-2,2'-bibenzothiophene was determined to be 73%.

Example 10 (Scheme 14): Aerobic Pd-Catalyzed Oxidative Homocoupling of 3-Bromobenzothiophene to Give 3,3'-Dibromo-2,2'-Bibenzothiophene

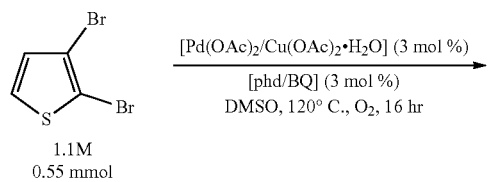

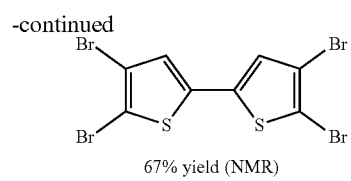

67% yield (NMR)

The same procedure as Example 7 was used, except that 2,3-dibromothiophene (133 mg, 0.55 mmol) was used instead of 4-bromothiazole, 3.7 mg Pd(OAc)$_2$ (0.017 mmol) was added, 200 µL (0.016 mmol) of the Cu(OAc)$_2$·H$_2$O/phd/BQ stock solution was added, and 237.5 µL additional DMSO was added. The $^1$H NMR yield of 4,4',5,5'-tetrabromo-2,2'-bithiophene was determined to be 67%.

Example 11: Monodentate Ligand Screening

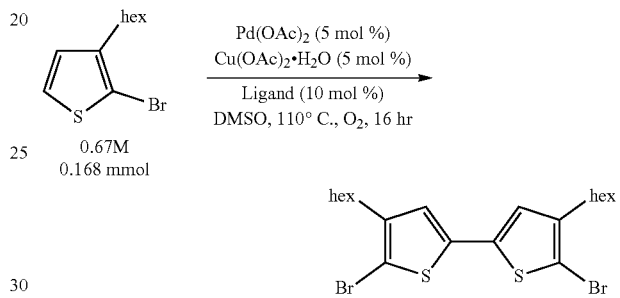

The individual ligands (10 mol %) were added to 13×100 mm borosilicate glass heavy wall test tubes as listed in each Entry in Table 1 below. Stock solutions of Pd(OAc)$_2$ (87.8 mg, 0.391 mmol, 39.1 mM) in 10.0 mL DMSO and Cu(OAc)$_2$·H$_2$O (78.0 mg, 0.391 mmol, 39.1 mM) in 10.0 mL DMSO were created, and 0.215 mL of each stock solution (0.0084 mmol) was added to each tube. Then, 2-bromo-3-hexylthiophene (34.0 µL, 0.168 mmol) was added to each tube. The reactions were then placed in an orbital mixing block with heating element and run in the same way as in Example 1, except at 110° C. instead of 120° C. After 16 hours, the reactions were stopped, and after cooling, they were worked up in the same way as Example 1 for HPLC analysis.

The recovered starting material 2-bromo-3-hexylthiophene was also quantified by HPLC analysis against a calibration curve of 2-bromo-3-hexylthiophene and phenanthrene standard. The results are shown in Table 1.

TABLE 1

Monodentate Ligand Screening at 110° C.

| Entry | Ligand Chemdraw | Ligand name | Mass Balance (%) | Recovered Starting Mat. (%) | 2,2'-Bithiophene Yield (%) |
|---|---|---|---|---|---|
| 1 | NMe$_2$-pyridine | 4-dimethylamino-pyridine | 78 | 21 | 57 |

TABLE 1-continued

Monodentate Ligand Screening at 110° C.

| Entry | Ligand Chemdraw | Ligand name | Mass Balance (%) | Recovered Starting Mat. (%) | 2,2'-Bithiophene Yield (%) |
|---|---|---|---|---|---|
| 2 | OMe | 4-methoxypyridine | 62 | 15 | 47 |
| 3 | tBu | 4-tert-butylpyridine | 62 | 19 | 43 |
| 4 | | Pyridine | 54 | 8 | 46 |
| 5 | F | 3-fluoropyridine | 34 | 5 | 29 |
| 6 | Me | 3-methylpyridine | 40 | 14 | 26 |
| 7 | Cl | 3-chloropyridine | 35 | 7 | 28 |
| 8 | | 4-acetylpyridine | 70 | 37 | 33 |
| 9 | O$_2$N | 3-nitropyridine | 36 | 12 | 24 |
| 10 | MeO | 2-methoxypyridine | 35 | 10 | 25 |
| 11 | HO | 2-hydroxypyridine | 37 | 16 | 21 |
| 12 | | Quinoline | 65 | 30 | 35 |
| 13 | None | None | 36 | 13 | 23 |

Example 12: Bidentate Ligand Screening

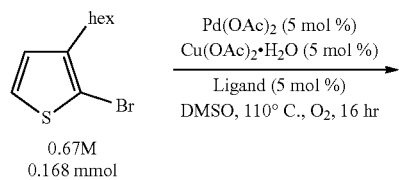 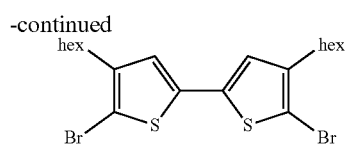

The individual ligands (5 mol %) were added to 13×100 mm borosilicate glass heavy wall test tubes as listed in each Entry in Table 2. Stock solutions of Pd(OAc)$_2$ (87.8 mg, 0.391 mmol, 39.1 mM) in 10.0 mL DMSO and Cu(OAc)$_2$·H2O (78.0 mg, 0.391 mmol, 39.1 mM) in 10.0 mL DMSO were created, and 0.215 mL of each stock solution (0.0084 mmol) was added to each tube. Then, 2-bromo-3-hexylthiophene (34.0 μL, 0.168 mmol) was added to each tube. The reactions were then placed in an orbital mixing block with heating element and run in the same way as in Example 1, except at 110° C. instead of 120° C. After 16 hours, the reactions were stopped, and after cooling, they were worked up in the same way as Examples 1 and 11 for HPLC analysis.

TABLE 2

Bidentate Ligand Screening at 110° C.

| Entry | Ligand Chemdraw | Ligand name | Mass Balance (%) | Recovered Starting Mat. (%) | 2,2'-Bithiophene Yield (%) |
|---|---|---|---|---|---|
| 1 | | 4,5-diazafluoren-9-one | 40 | 14 | 26 |
| 2 | | 4,4'-di-tert-butyl-2,2'-bipyridine | 82 | 38 | 44 |
| 3 | | 4,4'-dimethoxy-2,2'-bipyridine | 82 | 36 | 46 |
| 4 | | 5,5'-dimethoxy-2,2'-bipyridine | 88 | 41 | 47 |
| 5 | | 2,2'-biquinoline | 91 | 44 | 47 |
| 6 | | 4,4'-bis(trifluoromethyl)-2,2'-bipyridine | 71 | 14 | 57 |
| 7 | | 2,2'-biquinoline | 44 | N/A | 44 |

TABLE 2-continued

Bidentate Ligand Screening at 110° C.

| Entry | Ligand Chemdraw | Ligand name | Mass Balance (%) | Recovered Starting Mat. (%) | 2,2'-Bithiophene Yield (%) |
|---|---|---|---|---|---|
| 8 | | 1,10-phenanthroline | 82 | 34 | 48 |
| 9 | | 4,7-diphenyl-2,9-dimethyl-1,10-phenanthroline | 87 | 44 | 43 |
| 10 | | 2,9-dimethyl-1,10-phenanthroline | 57 | 21 | 36 |
| 11 | | 4,7-diphenyl-2,9-dimethyl-1,10-phenanthroline | 51 | 16 | 35 |
| 12 | | 1,2-Bis-((2,4,6-trimethylphenyl)imino)acenaphthene | 65 | 30 | 35 |
| 13 | | 1,2-Bis-((4-methylphenyl)imino)acenaplithene | 53 | 18 | 35 |
| 14 | | 6,6'-dimethoxy-2,2'-bipyridine | 34 | 11 | 23 |
| 15 | | 2,2'-bipyrimidine | 58 | 1 | 57 |
| 16 | | 1,10-phenanthroline-5,6-dione | 88 | 8 | 80 |

TABLE 2-continued

Bidentate Ligand Screening at 110° C.

| Entry | Ligand Chemdraw | Ligand name | Mass Balance (%) | Recovered Starting Mat. (%) | 2,2'-Bithiophene Yield (%) |
|---|---|---|---|---|---|
| 17 | Ph₂P–PPh₂ | 1,2-bis(diphenylphosphino)ethane | 42 | 17 | 25 |
| 18 | (binaphthyl bisphosphine structure) | (±)-2,2'-bis(diphenylphosphino)-1,1'-binaphthalene | 31 | 7 | 24 |
| 19 | (ferrocene bisphosphine structure) | 1,1'-ferrocenediyl-bis(diphenylphosphine) | 41 | 27 | 14 |
| 20 | None | None | 36 | 13 | 23 |

Example 13: Ligand Screening at 111° C.

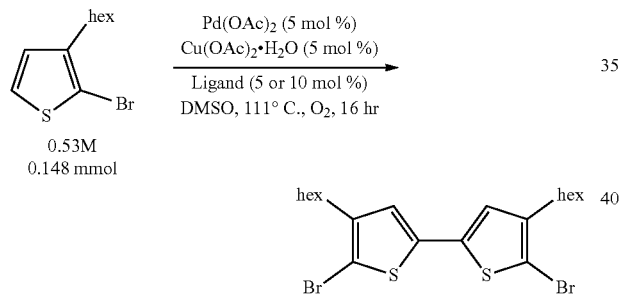

The individual ligands (5 or 10 mol %) were added to 13×100 mm borosilicate glass heavy wall test tubes as listed in each Entry in Table 3. For Entries 1-12, a stock solution of Pd(OAc)₂ (21.9 mg, 0.0976 mmol, 30.0 mM) and Cu(OAc)₂·H₂O (19.5 mg, 0.0977 mmol, 30.0 mM) in 3.25 mL DMSO was created, and 0.250 mL of the stock solution (0.0075 mmol) was added to each tube. For Entries 13-16, a stock solution of Pd(OAc)₂ (8.5 mg, 0.0379 mmol, 30.3 mM) and Cu(OTf)₂ (13.6 mg, 0.0376 mmol, 30.1 mM) in 1.25 mL DMSO was created, and 0.250 mL of the stock solution (0.0075 mmol) was added to each tube. Then, 2-bromo-3-hexylthiophene (30.0 µL, 0.148 mmol) was added to each tube. The reactions were then placed in an orbital mixing block with heating element and run in the same way as in Example 1, except at 111° C. instead of 120° C. After 16 hours, the reactions were stopped, and after cooling, they were worked up in the same way as Examples 1 and 11 for HPLC analysis. Results are shown in Table 3 below.

TABLE 3

Ligand Screening at 111° C.

| Entry | Ligand Chemdraw | Ligand name (mol %) | Mass Balance (%) | Recovered Starting Mat. (%) | 2,2'-Bithiophene Yield (%) |
|---|---|---|---|---|---|
| 1 | (bipyridine structure) | 2,2'-bipyridine (5) | 78 | 32 | 46 |
| 2 | (phenanthroline structure) | 1,10-phenanthroline (5) | 80 | 36 | 44 |

TABLE 3-continued

Ligand Screening at 111° C.

| Entry | Ligand Chemdraw | Ligand name (mol %) | Mass Balance (%) | Recovered Starting Mat. (%) | 2,2'-Bithiophene Yield (%) |
|---|---|---|---|---|---|
| 3 | | 1,10-phenanthroline-5,6-dione (5) | 79 | 5 | 74 |
| 4 | | 2,2'-bipyrimidine (5) | 61 | 1 | 60 |
| 5 | | 6-methyl-2,2'-bipyridine (5) | 60 | 17 | 43 |
| 6 | | 6,6'-dimethyl-2,2'-bipyridine (5) | 57 | 34 | 23 |
| 7 | | 4,4'-dimethoxy-2,2'-bipyridine (5) | 74 | 33 | 41 |
| 8 | | 4,4'-di-tert-butyl-2,2'-bipyridine (5) | 75 | 32 | 43 |
| 9 | | 4-dimethylamino-pyridine (10) | 65 | 19 | 46 |
| 10 | | 4-methoxypyridine (10) | 56 | 11 | 45 |
| 11 | | 3-nitropyridine (10) | 33 | 9 | 24 |
| 12 | | 2-fluoropyridine (10) | 31 | 10 | 21 |

TABLE 3-continued

Ligand Screening at 111° C.

| Entry | Ligand Chemdraw | Ligand name (mol %) | Mass Balance (%) | Recovered Starting Mat. (%) | 2,2'-Bithiophene Yield (%) |
|---|---|---|---|---|---|
| 13a | [1,10-phenanthroline-5,6-dione structure] | 1,10-phenanthroline-5,6-dione (5) | 90 | 74 | 16 |
| 14a | [2-fluoropyridine structure] | 2-fluoropyridine (10) | 47 | 39 | 8 |
| 15a | [4-dimethylamino-pyridine structure] | 4-dimethylamino-pyridine (10) | 58 | 18 | 40 |
| 16a | [2,2'-bipyridine structure] | 2,2'-bipyridine (5) | 77 | 31 | 46 |

$^{a}$Cu(OTf)$_2$ was used instead of Cu(OAc)$_2$•H$_2$O.

Example 14: Component Analysis Results

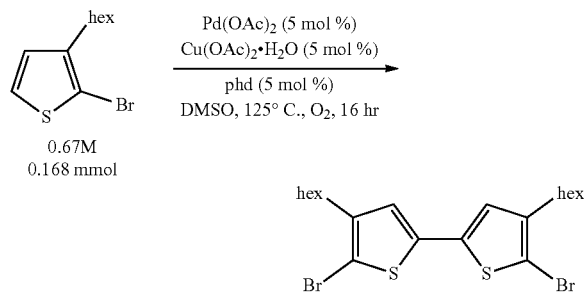

In this example, we demonstrate that all three of Pd(OAc)$_2$, Cu(OAc)$_2$, and phd are needed for efficient catalysis.

A stock solution of Pd(OAc)$_2$ (74.9 mg, 0.334 mmol, 38.8 mM) and phd (70.1 mg, 0.334 mmol, 38.8 mM) in 8.60 mL DMSO was created (after heating with stirring at 65° C. to dissolve the mixture). A stock solution of Cu(OAc)$_2$·H$_2$O (20.0 mg, 0.100 mmol, 38.5 mM) and phd (21.0 mg, 0.100 mmol, 38.5 mM) in 2.6 mL DMSO was created.

Entry 1: Solid Cu(OAc)$_2$·H$_2$O was added to a 13×100 mm borosilicate glass heavy wall test tube. Then, 0.215 mL (0.0083 mmol) of the Pd(OAc)$_2$/phd stock solution was added to the test tube.

Entry 2: 0.215 mL (0.0083 mmol) of the Pd(OAc)$_2$/phd stock solution was added to a 13×100 mm borosilicate glass heavy wall test tube.

Entry 3: 0.215 mL (0.0083 mmol) of the Cu(OAc)$_2$·H$_2$O/phd stock solution was added to a 13×100 mm borosilicate glass heavy wall test tube.

Entries 4-7: The individual catalyst components (5 mol % unless otherwise indicated) were added to 13×100 mm borosilicate glass heavy wall test tubes.

Then, 2-bromo-3-hexylthiophene (34.0 μL, 0.168 mmol) was added to each tube. The reactions were then placed in an orbital mixing block with heating element and run in the same way as in Example 1, except at 125° C. instead of 120° C. After 16 hours, the reactions were stopped, and after cooling, they were worked up in the same way as Examples 1 and 11 for HPLC analysis. Results are shown in Table 4 below.

TABLE 4

Component Analysis Results

| Entry | Components | Mass Balance (%) | Recovered Starting Mat. (%) | 2,2'-Bithiophene Yield (%) |
|---|---|---|---|---|
| 1 | Pd(OAc)$_2$, Cu(OAc)$_2$•H$_2$O, phd | 90 | 3 | 87 |
| 2 | Pd(OAoc)$_2$, phd | 99 | 88 | 11 |
| 4 | Cu(OAc)$_2$•H$_2$O, phd | 96 | 96 | 0 |
| 4 | Pd(OAc)$_2$•phd$^a$ | 99 | 92 | 7 |
| 5 | Cu(OAc)$_2$•H$_2$O, phd$^a$ | 97 | 97 | 0 |
| 6 | Pd(OAc)$_2$ | 76 | 71 | 5 |
| 7 | Cu(OAc)$_2$•H$_2$O | 95 | 95 | 0 |

$^a$= 2.5 mol % phd instead of 5 mol % phd

Example 15: Effect of Adding Benzoquinone or Tert-Butylbenzoquinone

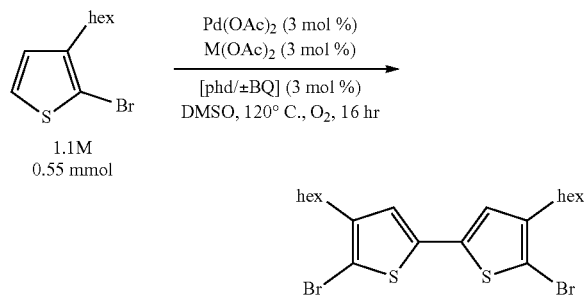

1.1M
0.55 mmol

Stock solutions of Pd(OAc)$_2$ (95.9 mg, 0.427 mmol, 85.4 mM) in 5.0 mL DMSO and phd (89.8 mg, 0.427 mmol, 85.4 mM) in 5.0 mL DMSO were created. The individual Components listed in Table 5 were added to the respective test tube. Then, 195 μL of each of the stock solutions was added to each test tube. Then, 2-bromo-3-hexylthiophene (112.5 μL, 0.555 mmol) was added to each test tube. The reactions were then placed in an orbital mixing block with heating element and run in the same way as in Example 1. After 16 hours, the reactions were stopped, and after cooling, they were worked up in the same way as Examples 1 and 11 for HPLC analysis. Results are shown in Table 5 below.

TABLE 5

Effect of Adding Benzoquinone or tert-Butylbenzoquinone

| Entry | Components | Mass Balance (%) | Recovered Starting Mat. (%) | 2,2'-Bithiophene Yield (%) |
|---|---|---|---|---|
| 1 | Cu(OAc)$_2$•H$_2$O | 93 | 11 | 82 |
| 2 | Cu(OAc)$_2$•H$_2$O, BQ | 99 | 2 | 97 |
| 3 | Cu(OAc)$_2$•H$_2$O, $^t$BuBQ | 96 | 1 | 95 |
| 4 | Ni(OAc)$_2$•4H$_2$O | 105 | 29 | 76 |
| 5 | Ni(OAc)$_2$•4H$_2$O, BQ | 105 | 58 | 47 |
| 6 | Ni(OAc)$_2$•4H$_2$O, $^t$BuBQ | 105 | 25 | 82 |

Example 16: Assessment of Copper Cocatalysts

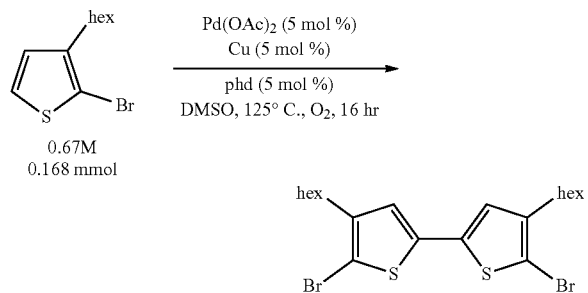

0.67M
0.168 mmol

The copper cocatalysts (5 mol %) were added to 13×100 mm borosilicate glass heavy wall test tubes as listed in each Entry in Table 6. Then, 0.215 mL (0.0083 mmol) of the Pd(OAc)$_2$/phd stock solution from Example 14 was added to each test tube. Then, 2-bromo-3-hexylthiophene (34.0 μL, 0.168 mmol) was added to each test tube. The reactions were then placed in an orbital mixing block with heating element and run in the same way as in Example 1, except at 125° C. instead of 120° C. After 16 hours, the reactions were stopped, and after cooling, they were worked up in the same way as Examples 1 and 11 for HPLC analysis. Results are shown in Table 6 below.

TABLE 6

Assessment of Copper Cocatalysts

| Entry | Copper Cocatalyst | Mass Balance (%) | Recovered Starting Mat. (%) | 2,2'-Bithiophene Yield (%) |
|---|---|---|---|---|
| 1 | Cu(OAc)$_2$•H$_2$O | 90 | 3 | 87 |
| 7 | CuSCN | 95 | 91 | 4 |
| 3 | Cu | 92 | 5 | 87 |
| 4 | CuCN | 83 | 10 | 73 |
| 5 | CuI | 59 | 27 | 32 |
| 6 | Cu$_2$O | 88 | 5 | 83 |
| 7 | CuSPh | 95 | 28 | 67 |
| 8 | Cu(3-ethyl-hexanoate) | 92 | 5 | 84 |
| 9 | Cu(OTf)$_2$ | 91 | 71 | 20 |
| 10 | Cu(acac)$_2$ | 87 | 38 | 49 |
| 11 | CuBr$_2$ | 89 | 80 | 9 |
| 12 | CuCl$_2$ | 96 | 75 | 21 |
| 13 | CuF$_2$ | 85 | 5 | 80 |
| 14 | Cu(TFA)$_2$•xH$_2$O | 66 | 38 | 28 |
| 15 | Cu(3-methyl-salicylate) | 98 | 15 | 83 |
| 16 | CuCl | 95 | 32 | 63 |
| 17 | CuBr•SMe$_2$ | 92 | 47 | 45 |
| 18 | Cu(NO$_3$)$_2$•2H$_2$O | 86 | 64 | 22 |
| 19 | Cu(OAc) | 86 | 4 | 82 |
| 20 | CuO | 93 | 67 | 26 |
| 21 | CuCO$_3$•Cu(OH)$_2$ | 94 | 47 | 47 |

Example 17: Assessment of Other Metal Cocatalysts

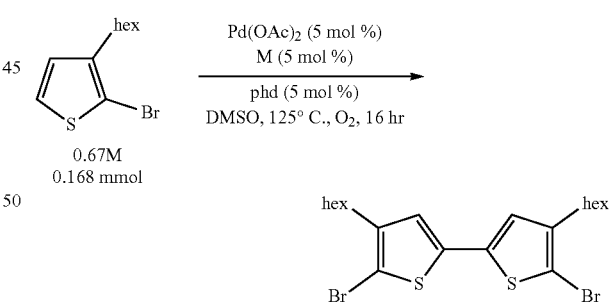

0.67M
0.168 mmol

The metal cocatalysts (5 mol %) were added to 13×100 mm borosilicate glass heavy wall test tubes as listed in each Entry in Table 7. Then, 0.215 mL (0.0083 mmol) of the Pd(OAc)$_2$/phd stock solution from Example 14 was added to each test tube. Then, 2-bromo-3-hexylthiophene (34.0 μL, 0.168 mmol) was added to each test tube. The reactions were then placed in an orbital mixing block with heating element and run in the same way as in Example 1, except at 125° C. instead of 120° C. After 16 hours, the reactions were stopped, and after cooling, they were worked up in the same way as Examples 1 and 11 for HPLC analysis. Results are shown in Table 7 below.

TABLE 7

Assessment of Other Metal Cocatalysts

| Entry | Metal Cocatalyst | Mass Balance (%) | Recovered Starting Mat. (%) | 2,2'-Bithiophene Yield (%) |
|---|---|---|---|---|
| 1 | Fe(NO$_3$)$_3$·9H$_2$O | 81 | 77 | 4 |
| 2 | Fe(OTf)$_3$ | 90 | 80 | 10 |
| 3 | Fe(OAc)$_2$ | 94 | 70 | 24 |
| 4 | Mn(OAc)$_2$·4H$_2$O | 92 | 8 | 84 |
| 5 | Ni(OAc)$_2$·4H$_2$O | 93 | 3 | 90 |
| 6 | Co(OAc)$_2$ | 81 | 28 | 53 |
| 7 | AgNO$_3$ | 94 | 52 | 42 |
| 8 | AgOAc | 100 | 82 | 18 |
| 9 | Al(NO$_3$)$_3$·9H$_2$O | 79 | 77 | 2 |
| 10 | Al(OTf)$_3$ | 97 | 88 | 9 |
| 11 | Ca(OAc)$_2$ | 94 | 47 | 47 |
| 12 | Mg(OAc)$_2$·4H$_2$O | 98 | 54 | 44 |

Example 18: Assessment of Palladium Catalysts

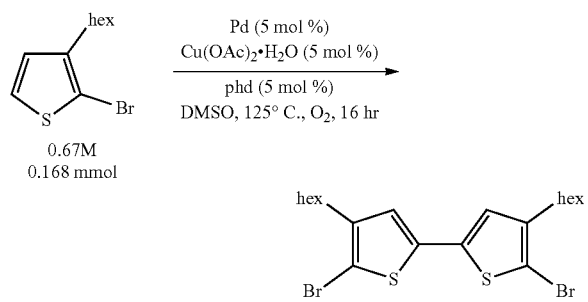

The palladium catalysts (5 mol %) were added to 13×100 mm borosilicate glass heavy wall test tubes as listed in each Entry in Table 8. Then, 0.215 mL (0.0083 mmol) of the Cu(OAc)$_2$·H$_2$O/phd stock solution from Example 14 was added to each test tube. Then, 2-bromo-3-hexylthiophene (34.0 µL, 0.168 mmol) was added to each test tube. The reactions were then placed in an orbital mixing block with heating element and run in the same way as in Example 1, except at 125° C. instead of 120° C. After 16 hours, the reactions were stopped, and after cooling, they were worked up in the same way as Examples 1 and 11 for HPLC analysis. Results are shown in Table 8 below.

TABLE 8

Assessment of Palladium Catalysts

| Entry | Palladium Source | Mass Balance (%) | Recovered Starting Mat. (%) | 2,2'-Bithiophene Yield (%) |
|---|---|---|---|---|
| 1 | Pd(OAc)$_2$ | 90 | 3 | 87 |
| 2 | Pd(TFA)$_2$ | 90 | 32 | 58 |
| 3 | Pd(O$_2$CC$_2$H$_5$)$_2$ | 86 | 1 | 85 |
| 4 | Pd(OPiv)$_2$ | 87 | 4 | 83 |
| 5 | PdI$_2$ | 63 | 48 | 15 |
| 6 | Pd(acac)$_2$ | 86 | 40 | 46 |
| 7 | Pd(OBz)$_2$ | 86 | 1 | 85 |
| 8 | PdO | 96 | 96 | 0 |
| 9 | Pd(NO$_3$)$_2$·2H$_2$O | 77 | 58 | 19 |
| 10 | Pd$_2$(dba)$_3$·CHCl$_3$ | 56 | 3 | 53 |

Example 19: Assessment of Literature Reaction Conditions: 50° C.

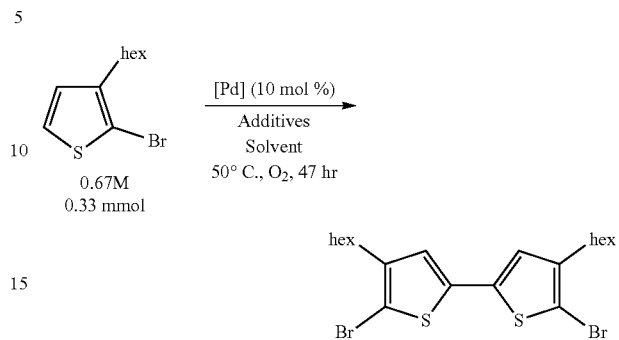

The individual catalyst components were added to 13×100 mm borosilicate glass heavy wall test tubes as listed in Table 9 and the conditions listed above. Then, 2-bromo-3-hexylthiophene (67.5 µL, 0.33 mmol) was added to the test tubes. Finally, solvent was added to each test tube. The reactions were then placed in an orbital mixing block with heating element and run in the same way as in Example 1, except at 50° C. instead of 120° C. After 47 hours, the reactions were stopped, and after cooling, dibromomethane (50 µL, 0.71 mmol) was added to each tube along with additional solvent. After filtering through Celite, the reactions were analyzed by $^1$H NMR spectroscopy against the dibromomethane standard. Results are in Table 9 below.

TABLE 9

Assessment of Literature Reaction Conditions: 50° C.

| Entry | Reaction Condition | Mass Balance (%) | Recovered Starting Mat. (%) | 2,2'-Bithiophene Yield (%) |
|---|---|---|---|---|
| 1 | Wang 2014 Org. Lett. (Aerobic Thiophene Homocoupling) | 55 | 55 | Trace |
| 2 | Stahl Unpublished Condition 1 (C2 indole arylation) | <56 | 51 | <5 |
| 3 | Stahl Unpublished Condition 2 (C3 indole arylation) | 56 | 51 | 5 |
| 4 | Stahl/Campbell C2 Indole Arylation | 81 | 68 | 13[a] |
|   | Stahl/Izawa o-xylene homocoupling | 68 | 68 | 0[b] |

Note:
the reactions were quantified by $^1$H NMR spectroscopy

[a] assignment of product (from $^1$H NMR) is uncertain

[b] The peaks in the $^1$H NMR spectrum are broad, so ruling out the presence of the desired product cannot be definitively done.

Wang 2014 Org. Lett. (Aerobic Thiophene Homocoupling): 10 mol % Pd(OAc)$_2$, 1.0 equiv trifluoroacetic acid, DMSO Stahl Unpublished Condition 1 (C2 indole arylation): 10 mol % Pd(OAc)$_2$, 10 mol % Fe(NO$_3$)$_3$·9H$_2$O, 20 mol % HOTs, DCE Stahl Unpublished Condition 2 (C3 indole arylation): 10 mol % Pd(OAc)$_2$, 10 mol % Cu(OAc)$_2$·H$_2$O, 10 mol % BQ, 10 mol % 2,2-bipyrimidine, 20 mol % HOTs, 1:1 AcOH:TFE Stahl/Campbell C2 indole arylation: 10 mol % Pd(OPiv)$_2$, 10 mol % 4,5-diazafluoren-9-one, propionic acid Stahl/Izawa o-xylene homocoupling: 10 mol % Pd(OAc)$_2$, 10 mol % Cu(OTf)$_2$, 20 mol % 2- fluoropyridine, 13 mol % trifluoroacetic acid, AcOH

Example 20: Assessment of Literature Conditions: 110° C.

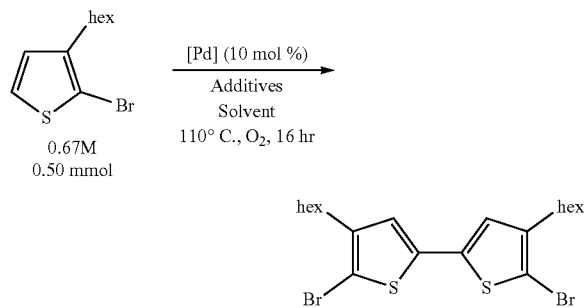

In this example, we assessed Literature Conditions at 110° C., after completion, and after all reactions sat at room temp. for four days before HPLC analysis.

The individual catalyst components were added to 13×100 mm borosilicate glass heavy wall test tubes as listed in Table 10 and the conditions listed above. Then, 2-bromo-3-hexylthiophene (67.5 µL, 0.33 mmol) was added to the test tubes. Finally, solvent was added to each test tube. The reactions were then placed in an orbital mixing block with heating element and run in the same way as in Example 1, except at 110° C. instead of 120° C. After 16 hours, the reactions were stopped. The test tubes were sealed with parafilm and rubber bands, they stood at room temperature for four days, and then they were worked up in the same way as Examples 1 and 11 for HPLC analysis. Results are shown in Table 10 below.

TABLE 10

Assessment of Literature Conditions

| Entry | Reaction Condition | Mass Balance (%) | Recovered Starting Mat. (%) | 2,2'-Bithiophene Yield (%) |
|---|---|---|---|---|
| 1 | Wang 2014 Org. Lett. (Aerobic Thiophene Homocoupling) | 61 | 59 | 2 |
| 2 | Stahl Unpublished Condition 1 (C2 indole arylation) | 40 | 38 | 2 |
| 3 | Stahl Unpublished Condition 2 (C3 indole arylation) | 56 | 56 | Trace |
| 4 | Stahl/Campbell C2 Indole Arylation | 65 | 63 | 2 |
| 5 | Stahl/Izawa o-xylene homocoupling | 35 | 35 | 0 |
| 6 | 10 mol % [Catalyst 1] | 57 | Trace | 57 |
| 7 | 10 mol % [Catalyst 2] | 88 | Trace | 88 |
| 8 | 5 mol % [Catalyst 1] | 71 | 1 | 70 |
| 9 | 5 mol % [Catalyst 2] | 103 | 12 | 91 |
| 10 | 2.5 mol % [Catalyst 1] | 94 | 57 | 37 |
| 11 | 2.5 mol % [Catalyst 2] | 100 | 56 | 44 |

Wang 2014 Org. Lett. (Aerobic Thiophene Homocoupling): 10 mol % Pd(OAc)$_2$, 1.0 equiv trifluoroacetic acid, DMSO
Stahl Unpublished Condition 1 (C2 indole arylation): 10 mol % Pd(OAc)$_2$, 10 mol % Fe(NO$_3$)$_3$•9H$_2$O, 20 mol % HOTs, propionic acid
Stahl Unpublished Condition 2 (C3 indole arylation): 10 mol % Pd(OAc)$_2$, 10 mol % Cu(OAc)$_2$•H$_2$O, 10 mol % BQ, 5 mol % 2,2-bipyrimidine, 20 mol % HOTs, propionic acid
Stahl/Campbell C2 indole arylation: 10 mol % Pd(OPiv)$_2$, 10 mol % 4,5-diazafluoren-9-one, propionic acid
Stahl/Izawa o-xylene homocoupling: 10 mol % Pd(OAc)$_2$, 10 mol % Cu(OTf)$_2$, 20 mol % 2-fluoropyridine, 13 mol % trifluoroacetic acid, propionic acid
Catalyst 1: Pd(OAc)$_2$, Cu(OAc)$_2$•H$_2$O, 2,2'-bipyridine
Catalyst 2: Pd(OAc)$_2$, Cu(OAc)$_2$•H$_2$O, 1,10-phenanthroline-5,6-dione

Example 21: Assessment of Literature Conditions: 120° C.

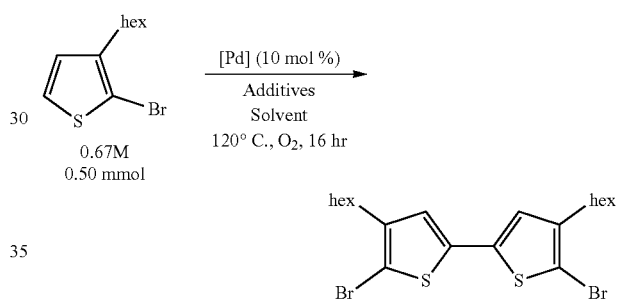

In this example, we assessed literature conditions as 120° C., where the reactions were worked up for HPLC analysis promptly after completion.

The individual catalyst components were added to 13×100 mm borosilicate glass heavy wall test tubes. Then, 2-bromo-3-hexylthiophene (67.5 µL, 0.33 mmol) was added to the test tubes. Finally, solvent was added to each test tube. The reactions were then placed in an orbital mixing block with heating element and run in the same way as in Example 1. After 16 hours, the reactions were stopped, and after cooling, they were worked up in the same way as Examples 1 and 11 for HPLC analysis. Results are shown in Table 11 below.

TABLE 11

Assessment of Literature Conditions: 120° C.

| Entry | Reaction Condition | Mass Balance (%) | Recovered Starting Mat. (%) | 2,2'-Bithiophene Yield (%) |
|---|---|---|---|---|
| 1 | Wang 2014 Org. Lett. (Aerobic Thiophene Homocoupling) | 67 | 67 | 0 |
| 2 | Stahl Unpublished Condition 1 (C2 indole arylation) | 32 | 32 | Trace |
| 3 | Stahl/Campbell C2 Indole Arylation | 74 | 72 | 2 |

TABLE 11-continued

| | Assessment of Literature Conditions: 120° C. | | | |
|---|---|---|---|---|
| Entry | Reaction Condition | Mass Balance (%) | Recovered Starting Mat. (%) | 2,2'-Bithiophene Yield (%) |
| 4 | Stahl/Izawa o-xylene homocoupling | 70 | 70 | Trace |
| 5 | 10 mol % [Catalyst 2] | 85 | 1 | 84 |

Wang 2014 Org. Lett. (Aerobic Thiophene Homocoupling): 10 mol % Pd(OAc)$_2$, 1.0 equiv trifluoroacetic acid, DMSO
Stahl Unpublished Condition 1 (C2 indole arylation): 10 mol % Pd(OAc)$_2$, 10 mol % Fe(NO$_3$)$_3$•9H$_2$O, 20 mol % HOTs, propionic acid
Stahl/Campbell C2 indole arylation: 10 mol % Pd(OPiv)$_2$, 10 mol % 4,5-diazafluoren-9-one, propionic acid
Stahl/Izawa o-xylene homocoupling: 10 mol % Pd(OAc)$_2$, 10 mol % Cu(OTf)$_2$, 20 mol % 2- fluoropyridine, 13 mol % trifluoroacetic acid, propionic acid
Catalyst 2: Pd(OAc)$_2$, Cu(OAc)$_2$•H$_2$O, 1,10-phenanthroline-5,6-dione

Example 22: Solvent Screen of Stahl Unpublished Condition 2: 120° C.

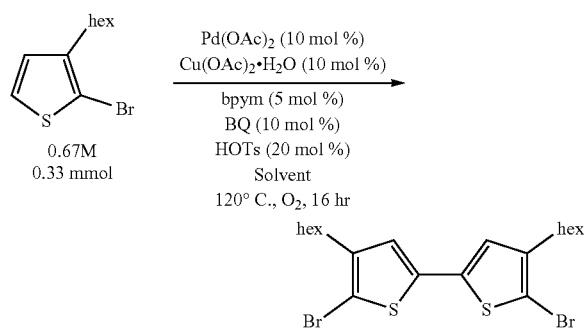

The individual catalyst components were added to 13×100 mm borosilicate glass heavy wall test tubes as listed above. Then, 2-bromo-3-hexylthiophene (67.5 μL, 0.33 mmol) was added to the test tubes. Finally, solvent (0.43 mL) was added to each test tube as listed in Table 12. The reactions were then placed in an orbital mixing block with heating element and run in the same way as in Example 1. After 16 hours, the reactions were stopped, and after cooling, they were worked up in the same way as Examples 1 and 11 for HPLC analysis. Results are shown in Table 12 below.

TABLE 12

| | Solvent Screen of Stahl Unpublished Condition 2: 120° C. | | | |
|---|---|---|---|---|
| Entry | Solvent | Mass Balance (%) | Recovered Starting Mat. (%) | 2,2'-Bithiophene Yield (%) |
| 1 | DMSO | 69 | 58 | 11 |
| 2 | DMF | 61 | 42 | 19 |
| 3 | DMA | 25 | 18 | 7 |
| 4 | NMP | 72 | 69 | 3 |
| 5 | Propylene carbonate | 51 | 51 | Trace |
| 6 | Propionic acid | 0 | 0 | 0 |

Stahl Unpublished Condition 2 (C3 indole arylation): 10 mol % Pd(OAc)$_2$, 10 mol % Cu(OAc)$_2$•H$_2$O, 10 mol % BQ, 5 mol % 2,2-bipyrimidine, 20 mol % HOTs, solvent

Example 23: Discovery of 1,10-Phenanthroline-5,6-Dione as an Effective Ancillary Ligand for Aerobic Oxidative Pd-Catalyzed Thiophene C—H Homocoupling with Relevance to Organic Materials Synthesis In this example, we extend the results reported in Examples 1-22, and provide additional supporting details. Specifically, we report the Pd/Cu-cocatalyzed aerobic oxidative C—H homocoupling of a variety of thiophenes and other heterocycles relevant to organic materials synthesis. 1,10-phenanthroline-5,6-dione (phd) has been discovered to be an effective ligand in aerobic Pd catalysis.

Given our longstanding interest in aerobic C—H/C—H biaryl coupling, a method for the homocoupling of 2-bromo-3-hexylthiophene 1a (FIG. 5) was targeted. A variety of conditions for aerobic C—H/C—H biaryl coupling developed in our lab and elsewhere were screened but were found to be ineffective. Conditions inspired by the aerobic Pd-catalyzed C—H homocoupling of o-dimethylphthalate—including an ancillary ligand-supported Pd catalyst with a Cu cocatalyst—were screened and found to be more effective for the formation of bithiophene 2a.

Figure 5:
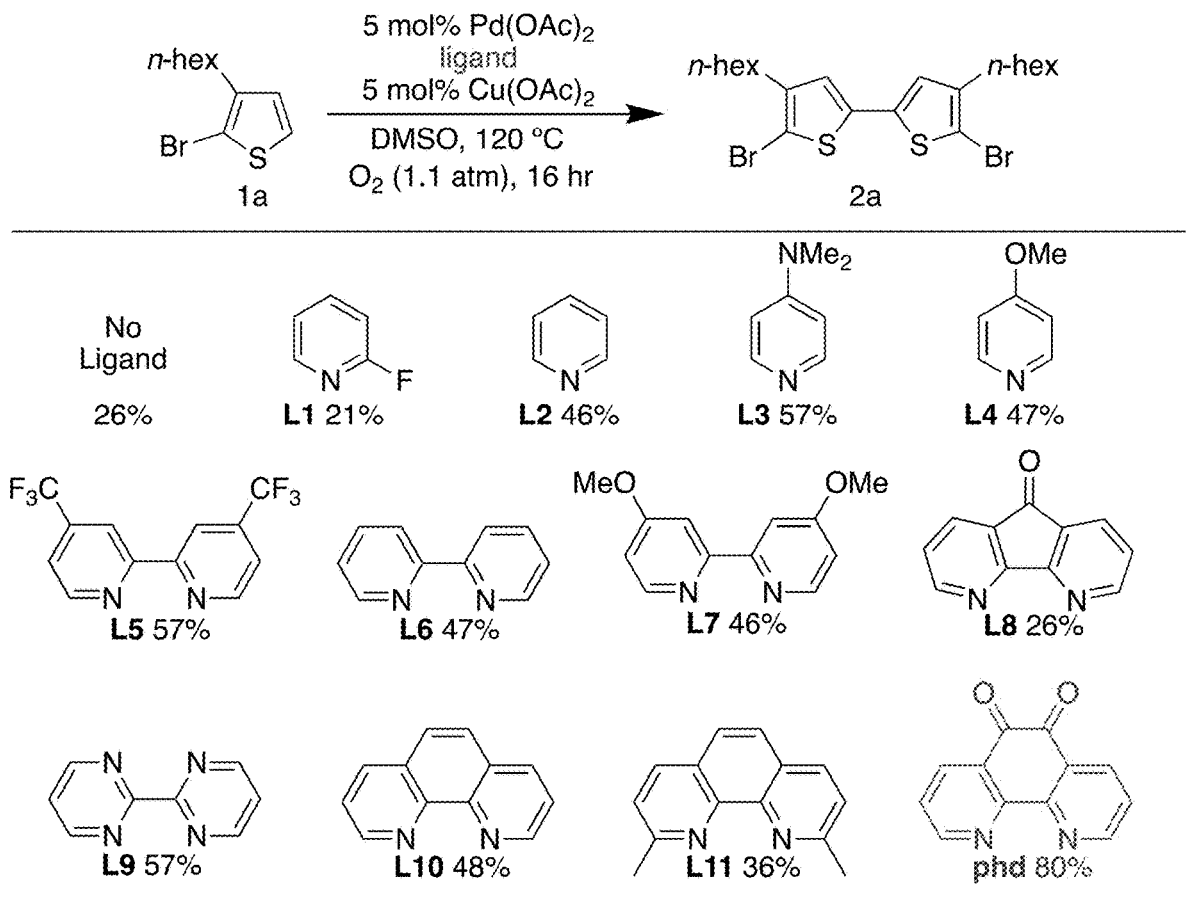
FIG. 5 is a chart showing the ligand effects in the Pd/Cu-cocatalyzed aerobic homocoupling of 2-Bromo-3-Hexylthiophene, the reaction scheme shown on the top line. Ligands and associated % yield of the desired product are shown in in the bottom three lines. Reaction conditions: 2-bromo-3-hexylthiophene (0.168 mmol), 5 mol % Pd(OAc)$_2$ (0.0084 mmol), 5 mol % Cu(OAc)$_2$·H$_2$O (0.0084 mmol), 10 mol % ligand (0.0168 mmol), 0.25 mL in DMSO, 1.1 atm pO$_2$, 16 hr. Reaction yields were determined by HPLC with a standard of phenanthrene in THF added after the reaction had cooled to room temperature.

It was found that use of electron-rich pyridines L3 offered significant increases in yields of 2a over electron-poor pyridines like L1. Bidentate nitrogen-donor ligands like 1,10-phenanthroline L10 generally afforded yields of approximately 45-50%, although introducing steric bulk in the ortho position (L11) provided diminished yields. A boost to 58% yield was enabled through use of 2,2'-bipyrimidine (bpym) L9, although this ligand gave low selectivity for desired product 2a, with almost complete starting material consumption. The optimal ligand was discovered to be 1,10-phenanthroline-5,6-dione (phd), which gave 80% yield of the desired product (FIG. 5).

Pd salts with anions more weakly coordinating than acetate were ineffective. Likewise, Cu salts with weakly coordinating anions were less effective compared to their more strongly coordinating counterparts. The addition of organic acids, which have been shown to promote other aerobic C—H/C—H biaryl couplings, greatly diminished product formation.

Metal additives other than CO salts have been shown to be effective for Pd-catalyzed C—H oxidation reactions. Notably, a number of co-catalytic additives not traditionally employed in aerobic Pd-catalyzed oxidation reactions were found to be effective at promoting the homocoupling relative to no additive, including Bi(OAc)$_3$, Zn(OAc)$_2$, and Mg(OAc)$_2$. In general, however, transition metal additives were found to be more effective, with Mn(OAc)$_2$ and Cu(OAc)$_2$ being the most effective, followed by Ni(OAc)$_2$. Iron(II) acetate and Co(OAc)$_2$ were less effective, although still promoted the homocoupling relative to no additive. Metal additives with anions less coordinating than acetate were less effective, consistent with observations regarding the anion on Pd and Cu. Ultimately, Cu(OAc)$_2$ was selected as the final cocatalyst, proving to be the most effective additive across a range of thiophene substrates tested (see Table 13 below).

TABLE 13

Metal Additive Effects in Pd/Cu-Cocatalyzed Aerobic C—H Homocoupling of 2-Bromo-3 Hexylthiophene

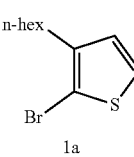

| M(OAc)$_n$ | Yield 2a (%) | M(OAc)$_n$ | Yield 2a (%) |
|---|---|---|---|
| — | 6 | Mn(OAc)$_2$ | 74 |
| CsOAc | 17 | Fe(OAc)$_2$ | 12 |
| Bi(OAc)$_3$ | 24 | Co(OAc)$_2$ | 40 |
| Mg(OAc)$_2$ | 35 | Ni(OAc)$_2$ | 66 |
| Ca(OAc)$_2$ | 12 | Cu(OAc)$_2$ | 73 |
| Sr(OAc)$_2$ | 10 | Zn(OAc)$_2$ | 30 |

Conditions: 1a (0.275 mmol, 55.0 µL), Pd(OAc)$_2$ (0.00825 mmol), phd (0.00825 mmol), M(OAc)$_n$ (0.00825 mmol), total volume of 0.25 mL in DMSO, 1.1 atm pO$_2$, 120° C., 16 hr. Reaction yield determined by $^1$H NMR against methyl-3,5-dinitrobenzoate internal standard.

The yield of 2a was improved to 90% when the loading of Pd(OAc)$_2$, phd, and Cu(OAc)$_2$ were lowered to 3 mol % with concomitant addition of 3 mol % of 1,4-benzoquinone (BQ).

Figure 6:
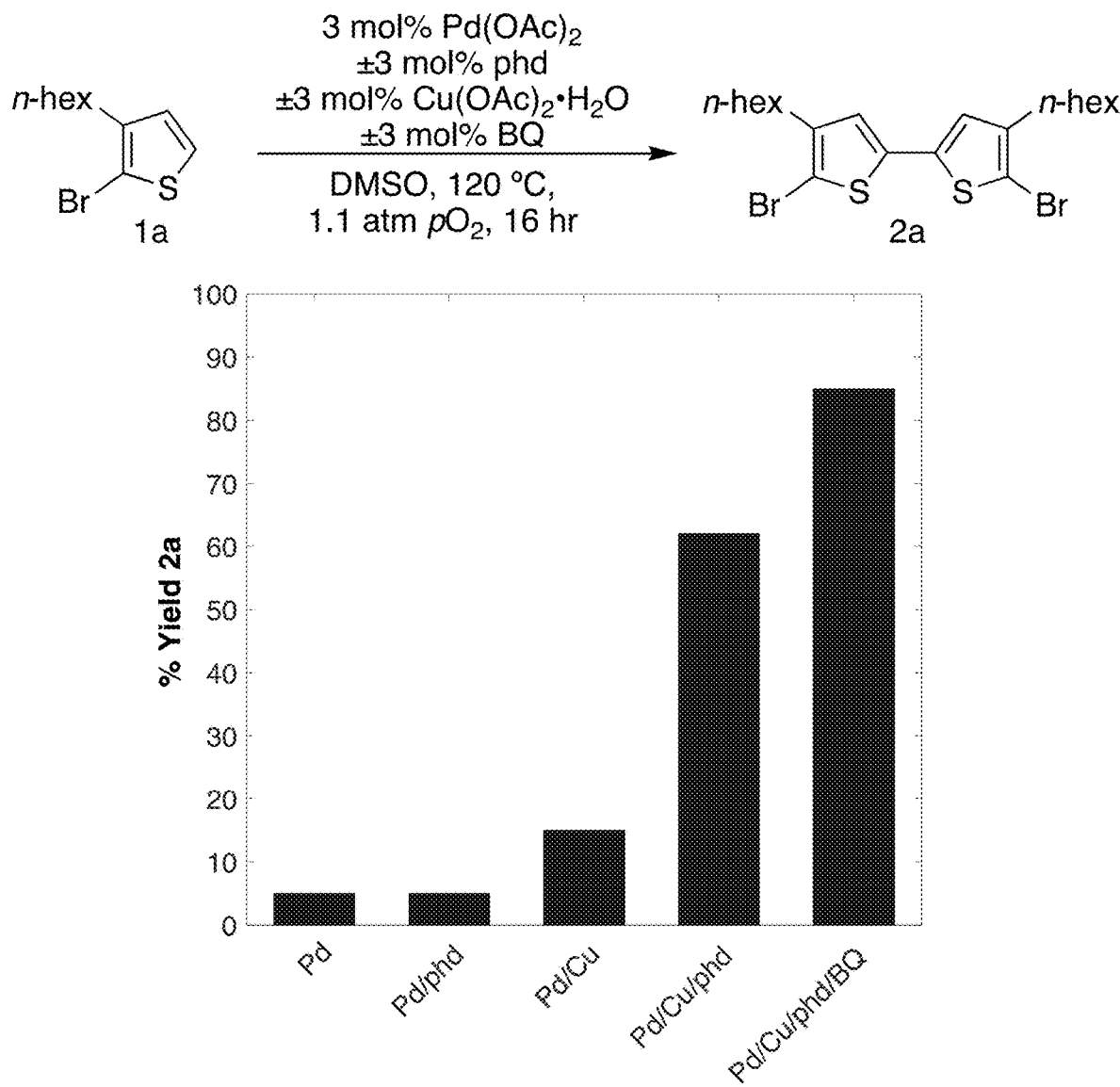
FIG. 6 includes a reaction scheme for thiophene C—H homocoupling (top) and a bar chart showing % yield as a function of the catalytic components used (bottom). Reaction conditions: 1a (1.1 mmol), catalyst (3 mol %), 1.0 mL in DMSO, 1.1 atm pO$_2$, 120° C., 16 hr.

In order to determine which components of the catalyst system were necessary for effective catalysis, a catalyst component screen was conducted (see FIG. 6). Pd(OAc)$_2$, Pd(OAc)$_2$/phd, and Pd(OAc)$_2$/Cu(OAc)$_2$ alone are ineffective at producing bithiophene in synthetically useful yields. High conversion of thiophene starting material is observed with Pd(OAc)$_2$/Cu(OAc)$_2$ but little product is obtained, suggesting phd promotes not only reactivity but also selectivity for product 2a. It is only the ternary mixture of Pd(OAc)$_2$/Cu(OAc)$_2$/phd that produces synthetically useful amounts of bithiophene, and addition of a catalytic amount of BQ further improves the yield by increasing catalyst lifetime.

Figure 7:
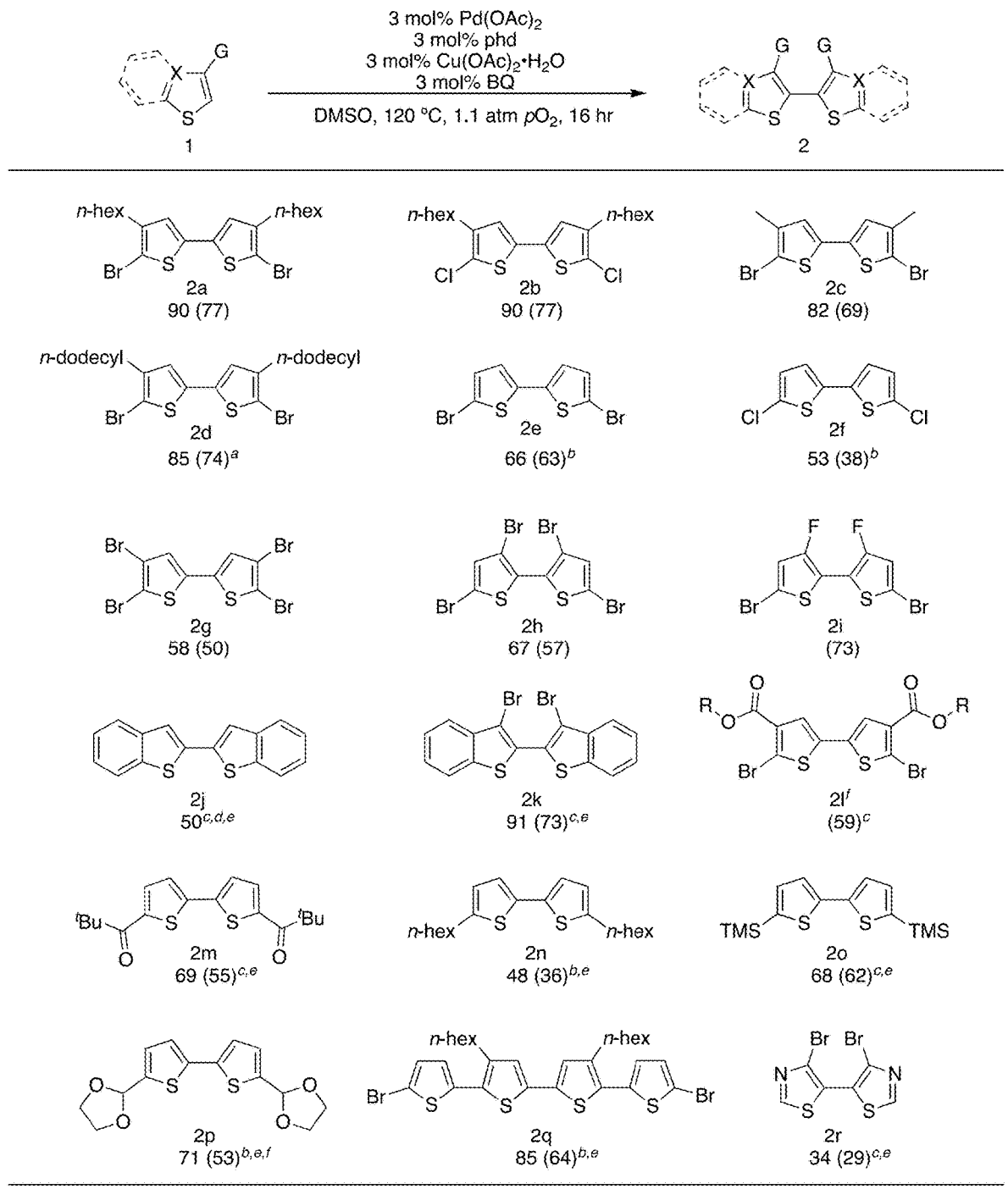
FIG. 7 is a chart showing the substrate scope for the aerobic C—H heteroarene homocoupling reaction scheme shown on the top line. Substrates and associated % yield of the desired product are shown in in the bottom six lines ($^1$H NMR yields shown with isolated yields in parentheses). Reaction conditions: Susbtrate (1.1 mmol, 1.1 M), 3 mol % each Pd(OAc)$_2$, phd, Cu(OAc)$_2$·H$_2$O, BQ, 1 mL reaction volume in DMSO, 120° C., 1.1 atm pO$_2$, 16 hr. $^a$Solvent was a 1.2:1 mixture DMSO:CyOAc. $^b$100° C. $^c$5 mol % catalyst.

The Pd(OAc)$_2$/phd/Cu(OAc)$_2$/BQ catalyst was then tested for the oxidative homocoupling of a series of thiophenes and related heterocycles (see FIG. 7). A variety of 2-halo-3-alkylthiophenes 1a-1c reacted smoothly to afford 2,2'-bithiophenes that are useful as intermediates or precursors to intermediates in materials synthesis in very good to excellent yields. In the course of isolating 2c, several milligrams of a purified byproduct 3c were obtained, which was found to be terthiophene 3c derived from the oxidative coupling of 1c and 2c. Similar $^1$H NMR spectroscopic signatures were observed in the crude reaction mixtures of other 2-halo-3-alkylthiophenes, suggesting other thiophenes may undergo this undesired overoxidation process, although no effort was made to isolate these putative over-oxidation products.

An 85% yield of 2d was obtained with use of the cosolvent cyclohexyl acetate, which likely helps solubilize 1d. Substrates 1e and 1f, which benefited from a lowered reaction temperature of 100° C., gave somewhat lower yields. Dihalogenated substrates gave moderate to good yields of products 2g-2i. Product 2i is noteworthy, as it has been found that fluorination in the 3 and 3' positions of the 2,2'-bithiophene moiety of an organic copolymer leads to improved solar cell power conversion efficiency. Benzo[b] thiophenes required higher catalyst loadings, with substrate 1j yielding 2j in 50% yield, while the 3-brominated analogue, 1k, coupled in 91% yield. The ester substrate 1l also required a higher catalyst loading to afford 2l, an intermediate towards an OSC, in 59% yield, while ketone 1m yielded product 2m in 69% yield.

Substrates 1n and 1o, possessing electron-donating groups in the 2 position, gave 48% and 68% spectroscopic yields of 2n and 2o, respectively. Substrate 1n required a lowered temperature of 100° C. for a synthetically useful yield. The acetal substrate 1p resulted in combined 71% yield of 2p and mono-deprotected 3p at 100° C.; a hydrolytic deprotection of these products would lead to 5,5'-bis(carb-aldehyde)-2,2'-bithiophene, a commonly used intermediate in reactions such as Knoevenagel condensations, Horner-Wadsworth-Emmons (HWE) olefinations, Wittig reactions, and other transformations. 2,2'-bithiophene substrate, 1q, was coupled in good spectroscopic yield of 85% at 100° C. to yield quaterthiophene 2q, suggesting that the catalyst shows promise for the synthesis of oligothiophene intermediates towards organic materials. 4-bromothiazole 1r showed only 34% spectroscopic yield of bithiazole 2r, which has been utilized as an intermediate for the synthesis of OFETs.

Figure 8A:
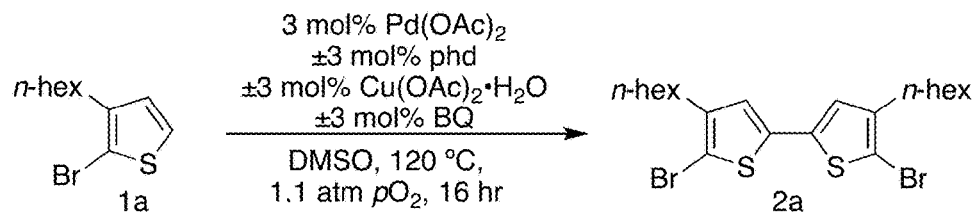
FIG. 8A is a reaction scheme for aerobic thiophene homocoupling.
Figure 8B:
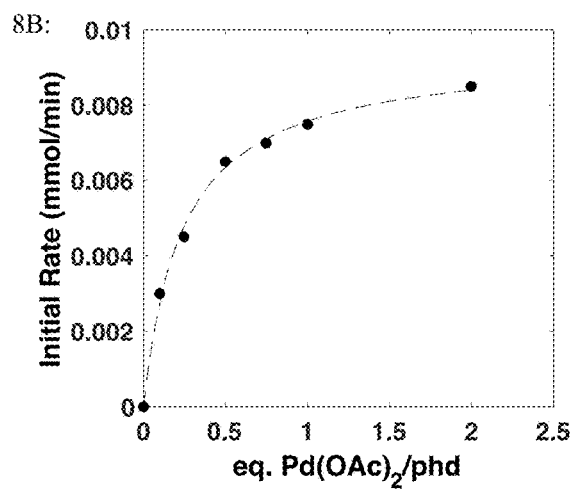
FIGS. 8B, 8C, 8D and 8E are graphs showing kinetic data for the aerobic thiophene C—H homocoupling shown in FIG. 8A, assessing the dependence on (8B) [Pd(OAc)$_2$/phd] (8C) [Cu(OAc)$_2$·H$_2$O] (8D) [phd] (1 and 4 equiv Cu(OAc)$_2$) and (8E) [1a]. Standard conditions: 33 mM catalyst ([Pd(OAc)$_2$], [Cu(OAc)$_2$·H$_2$O], [phd], [BQ]), 1.1 M [2a] (0.55 mmol), 1.1 atm pO$_2$, 0.50 mL in DMSO, 120° C. Standard conditions were employed, except for the concentration of the component being varied. Lines fit to the data are to guide the eye only.
Figure 8C:
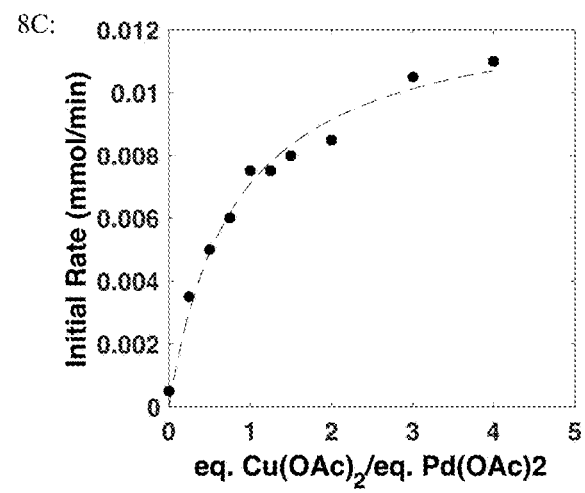
Figure 8D:
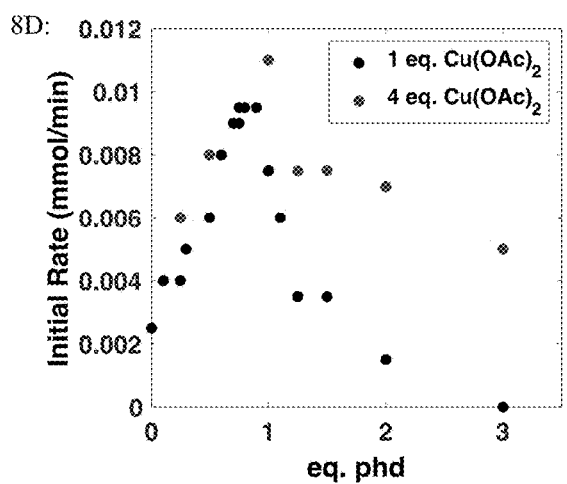
Figure 8E:
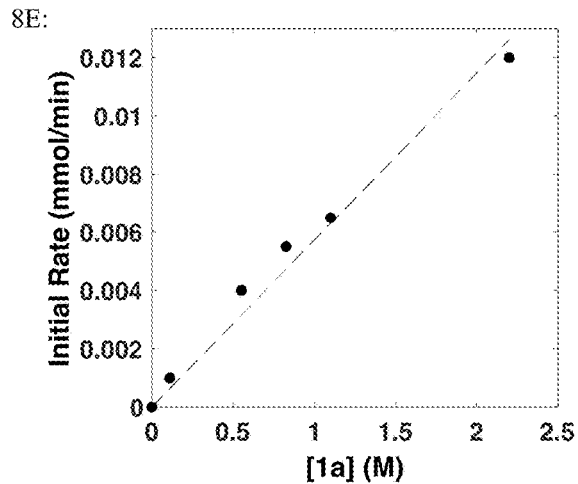

In order to gain mechanistic insight into the reaction (FIG. 8A), the dependence of the initial rate on the catalyst components was determined (see FIGS. 8B, 8C, 8D and 8E). Modulating the Pd(OAc)$_2$:phd ratio, the reaction rate increased in a 1$^{st}$ order fashion before maximizing at a Pd(OAc)$_2$:phd ratio of approximately 1:1. Pd(OAc)$_2$:phd ratios beyond 1:1 saw diminished rates, and catalysis was completely inhibited at a Pd(OAc)$_2$:phd ratio of 1:3. The rate maximum at a Pd(OAc)$_2$:phd ratio of 1:1 held at a Pd(OAc)$_2$:Cu(OAc)$_2$ ratio of 1:4, indicating phd preferentially binds Pd(OAc)$_2$ over Cu(OAc)$_2$ during the reaction, and that the active catalytic species is a 1:1 Pd(OAc)$_2$/phd complex.

The reaction was found to be 1$^{st}$ order in substrate (FIG. 8D) and zeroth order in [BQ] and pO$_2$, strongly suggesting the rate determining step is not oxidation of the catalyst. Saturation kinetics for [Pd(OAc$_2$)/phd] (FIG. 8B) and Cu(OAc)$_2$·H$_2$O was observed (FIG. 8C), and the onset of [Pd(OAc)$_2$/phd] saturation is delayed at elevated [Cu(OAc)$_2$] relative to [Pd(OAc)$_2$]. Such behavior indicates a preequilibrium association of Pd(OAc)$_2$/phd and Cu(OAc)$_2$ prior to the rate-limiting step. Given the extensive precedent of phd-supported multimetallic species (CITATION), such association seems even more credible. The exact nature of the rate-limiting step is unclear; however, based on literature precedent possible rate-limiting steps could include either C—H activation or transmetalation between two Pd-aryls. In either case, given that catalyst oxidation is not likely to be the rate-limiting step, Cu(OAc)$_2$ is likely serving to promote one of those steps.

C—H activation is a kinetically relevant step in the homocoupling reaction. Independent rates were measured for the homocoupling of 1a and 1a-D5 under standard conditions were measured, and h$_H$/k$_D$ was found to be 2.9, indicating at least partially rate-limiting C—H activation and consistent with KIEs of h$_H$/k$_D$ 2-5 observed in previously reported Pd-based oxidative biaryl coupling reactions. The ME was measured to be 2.4 and 2.5 at high and low [Cu(OAc)$_2$], respectively, suggesting that altering the Cu(OAc)$_2$ concentration does not affect the identity of the rate-limiting step.

Figure 9:
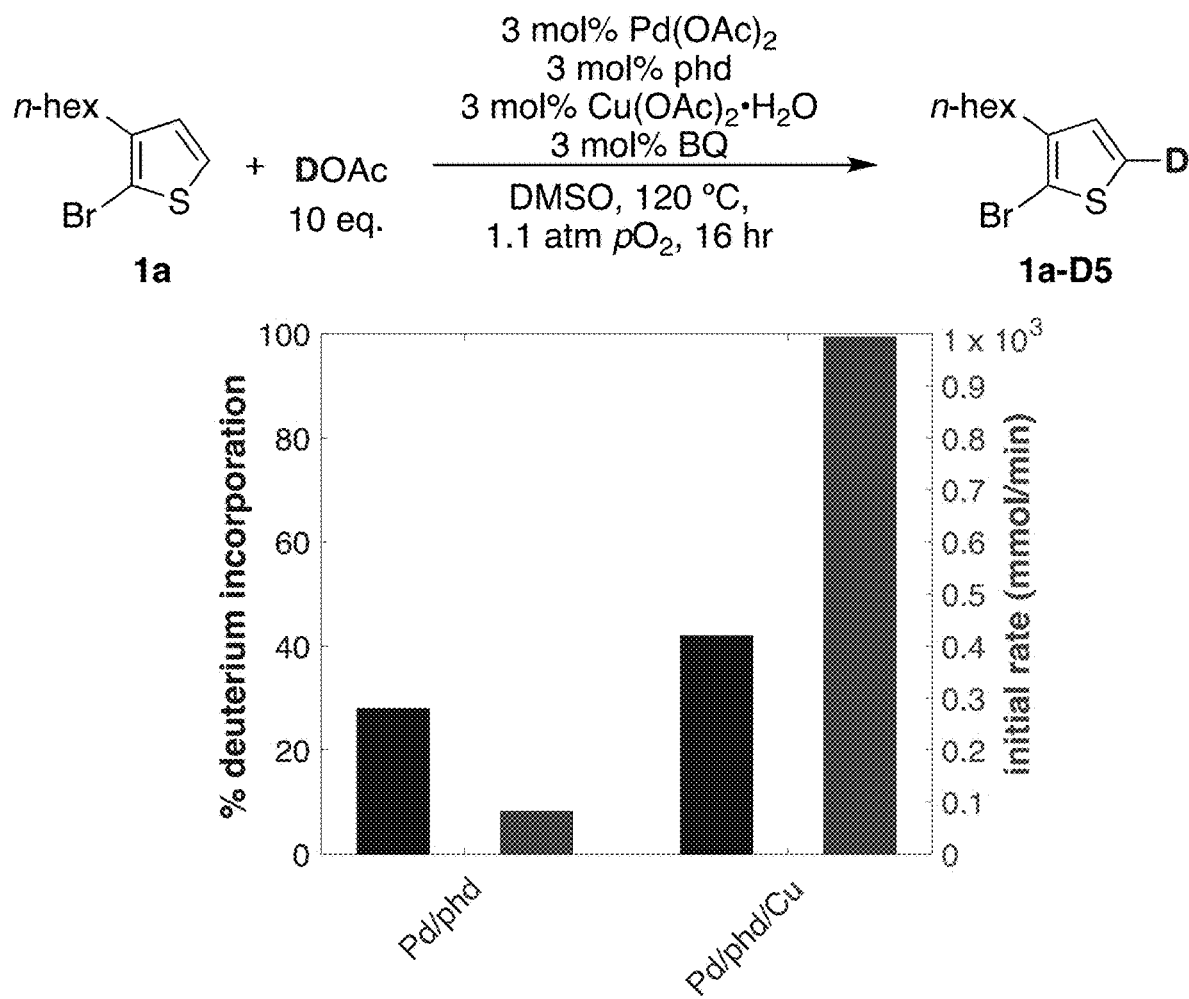
FIG. 9 shows the reaction scheme for thiophene H/D exchange (top) and a bar showing % D incorporation and rate of 2a formation (see FIG. 8A) when using both Pd(OAc)$_2$/phd and Pd(OAc)$_2$/phd/Cu(OAc)$_2$ catalytic systems. Data for 2a and 1a-D5 are reported for catalytic conditions with added DOAc. Conditions: 2a (1.1 mmol), catalyst (0.0165 mmol), BQ (0.0165 mmol), DOAc (11 mmol), 1.1 atm pO$_2$, 1.0 mL in DMSO-d$_6$, 120° C., 30 min.

To gain insight into the C—H activation step, 10 equiv DOAc (relative to substrate) were added to the reaction mixtures and allowed to react for 30 minutes (see FIG. 9). One or more components of the optimized catalyst system was systematically excluded, and the amount of deuterium incorporated into the starting material was measured.

FIG. 9 shows the yields of 1a-D5 and 2a, which forms in only small quantities under acidic conditions. No deuterium is incorporated into 1a when only $Cu(OAc)_2$ or $Cu(OAc)_2$/phd are used, while $Pd(OAc)_2$ alone and $Pd(OAc)_2$/Cu$(OAc)_2$ facilitated modest ($\geq 5\%$) deuterium incorporation. However, substantial deuterium incorporation values of 28% and 42% are observed by $^1H$ and $^2H$ NMR when $Pd(OAc)_2$/phd and $Pd(OAc)_2$/phd/$Cu(OAc)_2$ are used, respectively. While rates of deuterium incorporation by $Pd(OAc)_2$/phd and $Pd(OAc)_2$/phd/$Cu(OAc)_2$ are comparable, rates of product formation under standard conditions between the catalyst systems differ by nearly a factor of 10 in favor of the latter.

The discrepancy in rates of C—H activation vs. homocoupling suggests could be interpreted in several ways. If a sequential C—H activation mechanism on a single Pd center is operative, these data indicate that Cu is playing crucial role in one of the C—H activation steps but is largely inconsequential for the other C—H activation. If a transmetalation mechanism is operative, these data would be consistent with Cu promoting a transmetalation step between two Pd-aryls to form a Pd-biaryl that undergoes product-forming reductive elimination. Alternatively, $Cu(OAc)_2$ could serve to promote reductive elimination from a Pd-biaryl.

1,10-phenanthroline-4,5-dione is known to support the formation of multimetallic species wherein the phenanthroline moiety binds one metal and the o-quinone moiety binds another metal. This behavior prompted investigation into the speciation of the catalyst.

Figure 10A:
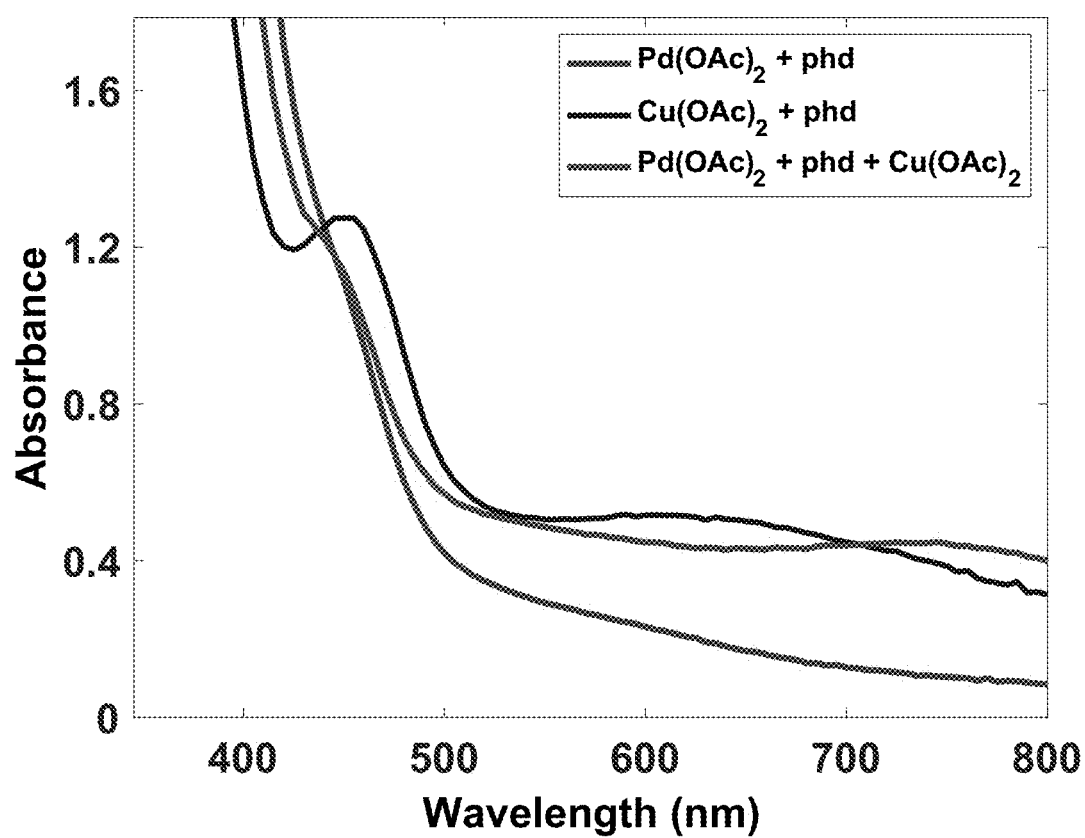
FIG. 10A shows UV/Vis spectra of Pd(OAc)$_2$/phd (red), Cu(OAc)$_2$/phd (blue), and Pd(OAc)$_2$/phd/Cu(OAc)$_2$ (green). Conditions: [Pd(OAc)$_2$]=16.5 mM, [Cu(OAc)$_2$]=16.5 mM, [phd]=16.5 mM.

UV/Vis spectra of 16.5 mM solutions of $Pd(OAc)_2$/phd, $Cu(OAc)_2$/phd, and $Pd(OAc)_2$/phd/$Cu(OAc)_2$ in DMSO are shown in FIG. 10A. $Pd(OAc)_2$/phd (FIG. 10A, red) contains a broad absorbance feature with an onset that begins at approximately 500 nm. $Cu(OAc)_2$/phd (FIG. 10A, blue) contains a broad feature centered at approximately 620 nm and a narrower feature at 460 nm. When $Pd(OAc)_2$, phd, and $Cu(OAc)_2$ are combined in equal ratios (FIG. 10A, green), the resulting spectrum contains a broad feature centered at approximately 730 nm and shoulder at approximately 450 nm. That is, a mixture of the three components results in a spectroscopically unique species that is neither $Pd(OAc)_2$/phd nor $Cu(OAc)_2$/phd. The precise nature of the interaction between $Pd(OAc)_2$, phd, and $Cu(OAc)_2$ is unclear, but potential modes of interaction include the binding of $Cu(OAc)_2$ to $Pd(OAc)_2$/phd via the o-quinone moiety or by bridging acetates.

Figure 10B:
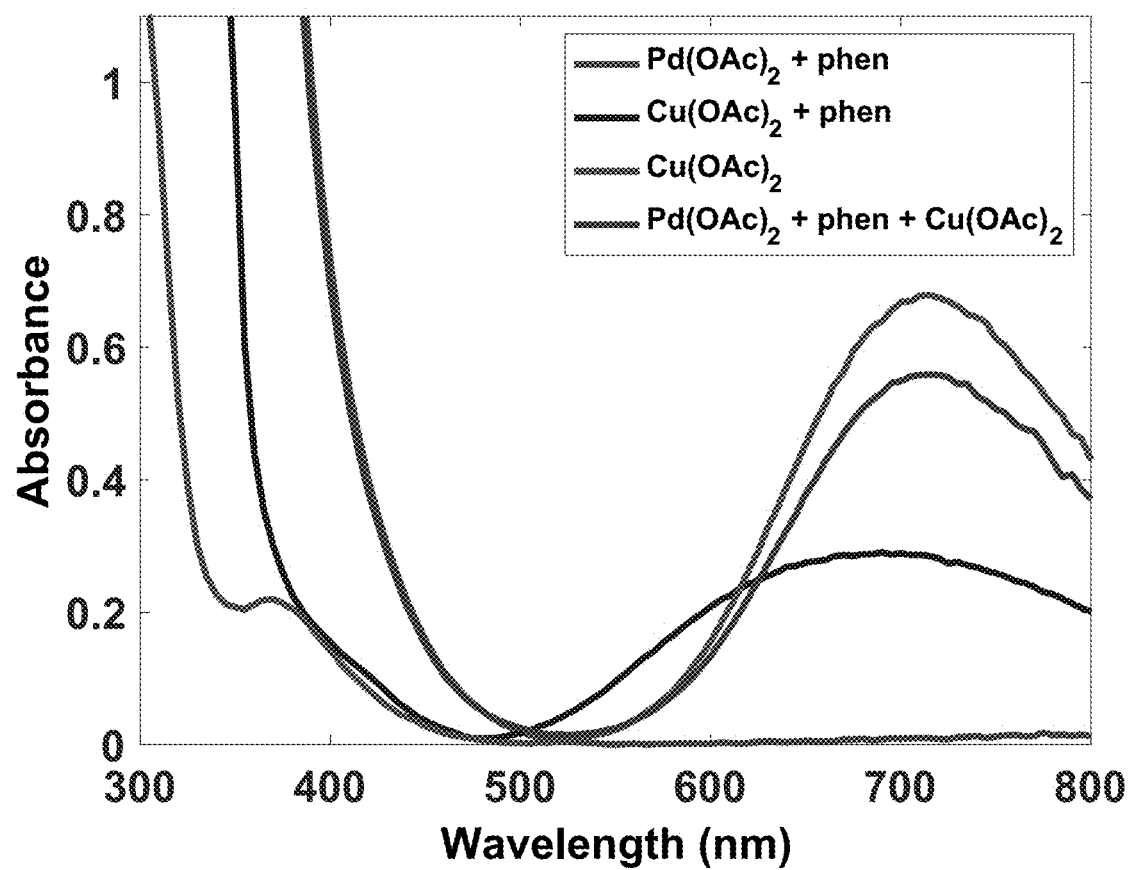
FIG. 10B shows UV/Vis spectra of Pd(OAc)$_2$/phenanthroline in DMSO (phen) (red), Cu(OAc)$_2$/phen (blue), Pd(OAc)$_2$/phen/Cu(OAc)$_2$ (purple) and Cu(OAc)$_2$ (green). Conditions: [Pd(OAc)$_2$]=16.5 mM, [Cu(OAc)$_2$]=16.5 mM, [phen]=16.5 mM in DMSO at room temperature.

In order to gain insight into the mode of ligand binding, similar experiments were conducted in which the structurally analogous phenanthroline ligand was used in lieu of phd. A 1:1 mixture of $Pd(OAc)_2$ and phen in DMSO (FIG. 10B, red) contains a strong absorbance onset at approximately 480 nm. $Cu(OAc)_2$/phen (FIG. 10B, blue) has a broad absorption feature centered at 490 nm, while $Cu(OAc)_2$ (FIG. 10B, green) has a broad absorbance at 710 nm. An equimolar mixture of $Pd(OAc)_2$, phenanthroline, and $Cu(OAc)_2$ (FIG. 10B, purple) contains a broad feature at 710 nm, and the onset of a strong absorbance at 480 nm. That is, the mixture of $Pd(OAc)_2$, phenanthroline, and $Cu(OAc)_2$ shows spectroscopic features consistent with phenanthroline-bound $Pd(OAc)_2$ and $Cu(OAc)_2$, indicating phenanthroline binds preferentially to $Pd(OAc)_2$ in the presence of $Cu(OAc)_2$ and that there is no association of $Cu(OAc)_2$ with $Pd(OAc)_2$/phen.

In sum, we have disclosed a method for the aerobic Pd and Cu cocatalyzed C—H/C—H homocoupling of thiophenes relevant to organic materials, using 1,10-phenanthroline-4,5-dione as an ancillary ligand, with phd being used as an effective ligand for an aerobic Pd-catalyzed oxidation reaction. A number of thiophenes relevant to organic materials are coupled in good to moderate yields under conditions that forego the need for a stoichiometric oxidant such as $Ag^I$ salts. Kinetic and mechanistic studies indicate that the $Cu(OAc)_2$ cocatalyst serves not to simply mediate the oxidation of $Pd^0$ to $Pd^{II}$, as it is traditionally assumed to do in aerobic Pd and Cu cocatalyzed oxidation reactions, but also serves to promote another step in the reaction. Several other metal additives not traditionally employed in aerobic Pd-catalyzed oxidation reactions were demonstrated to be competent for promoting the thiophene homocoupling. Spectroscopic evidence indicates the formation of multimetallic $Pd(OAc)_2$/phd/$M(OAc)_2$ species; however, the catalytic relevance of the species is unclear. The exact nature of promotional effect of Cu and other metal additives is the subject of ongoing study, but has important implications for the development of aerobic Pd-catalyzed C—H oxidation reactions.

The disclosure is not limited to the specific embodiments demonstrated in these examples. Instead, the scope of the invention is defined by the appended claims.

Endnote Citations:

[1] (a) Cheng, Y.-J.; Yang, S.-H.; Hsu, C.-S. *Chem. Rev.* 2009, 109, 5868-5923. (b) Mishra, A.; Bäuerle, P. *Angew. Chem., Int. Ed.* 2012, 51, 2020-2067.

[2] (a) Allard, S.; Forster, M.; Souharce, B.; Thiem, H.; Scherf, U. *Angew. Chem., Int. Ed.* 2008, 47, 4070-4098. (b) Facchetti, A. In *Handbook of Thiophene-Based Materials: Applications in Organic Electronics and Photonics*; Perepichka, I. F., Perepichka, D. F., Eds.; John Wiley & Sons, Ltd.: West Sussex, United Kingdom, 2009; p 595-646. (c) Usta, H.; Facchetti, A.; Marks, T. J. *Acc. Chem. Res.* 2011, 44, 501-510.

[3] Perepichka, I. F.; Perepichka, D. F.; Meng, H. In *Handbook of Thiophene-Based Materials: Applications in Organic Electronics and Photonics*; Perepichka, I. F., Perepichka, D. F., Eds.; John Wiley & Sons, Ltd.: West Sussex, United Kingdom, 2009; p 695-756.

[4] (a) Mishra, A.; Ma, C.-Q.; Bauerle, P. *Chem. Rev.* 2009, 109, 1141-1276. (b) Mishra, A.; Ma, C.-Q.; Segura, J. L.; Bäuerle, P. In *Handbook of Thiophene-Based Materials: Applications in Organic Electronics and Photonics*; Perepichka, I. F., Perepichka, D. F., Eds.; John Wiley & Sons, Ltd.: West Sussex, United Kingdom, 2009; p 1-155.

[5] Barbarella, G.; Zangoli, M.; Di Maria, F. In *Advances in Heterocyclic Chemistry*, Vol. 123; Scriven, E. F. V., Ramsden, C. A.; Elsevier Inc: 2017, p 105-167.

[6] Zhang, L.; Colella, N. S.; Cherniawski, B. P.; Mannsfeld, S. C. B.; Briseno, A. L. *ACS Appl. Mater. Interfaces* 2014, 6, 5327-5343.

[7] (a) Heeney, M.; Bailey, C.; Genevicius, K.; Shkunov, M.; Sparrowe, D.; Tierney, S.; McCulloch, I. *J. Am. Chem. Soc.* 2005, 127, 1078-1079. (b) Heeney, M.; Wagner, R.; McCulloch, I.; Tierney, S. World Patent 2005/111045 A1, 2005. (c) McCulloch, I.; Heeney, M.; Bailey, C.; Genevicius, K.; MacDonald, I.; Shkunov, M.; Sparrowe, D.; Tierney, S.; Wagner, R.; Zhang, W.; Chabinyc, M. L.; Kline, R. J.; McGehee, M. D.; Toney, M. F. *Nat. Mater.* 2006, 5, 328-333. (d) Chabinyc, M. L.; Toney, M. F.;

Kline, R. J.; McCulloch, I.; Heeney, M. *J. Am. Chem. Soc.* 2007, 129, 3226-3237. (e) DeLongchamp, D. M.; Kline, R. J.; Lin, E. K.; Fischer, D. A.; Richter, L. J.; Lucas, L. A.; Heeney, M.; McCulloch, I.; Northrup, J. E. *Adv. Mater.* 2007, 19, 833-837. (f) Kline, R. J.; DeLongchamp, D. M.; Fischer, D. A.; Lin, E. K.; Richter, L. J.; Chabinyc, M. L.; Toney, M. F.; Heeney, M.; McCulloch, I. *Macromolecules* 2007, 40, 7960-7965. (g) Hwang, I.-W.; Kim, J. Y.; Cho, S.; Yuen, J.; Coates, N.; Lee, K.; Heeney, M.; McCulloch, I.; Moses, D.; Heeger, A. J. *J. Phys. Chem. C* 2008, 112, 7853-7857.

[8] (a) Yuan, M.-C.; Chiu, M.-Y.; Liu, S.-P.; Chen, C.-M.; Wei, K.-H. *Macromolecules* 2010, 43, 6936-6938. (b) Su, M.-S.; Kuo, C.-Y.; Yuan, M.-C.; Jeng, U.-S.; Su, C.-J.; Wei, K.-H. *Adv. Mater.* 2011, 23, 3315-3319. (c) Su, Y.-W.; Liu, C.-M.; Jiang, J.-M.; Tsao, C.-S.; Cha, H.-C.; Jeng, U-S.; Chen, H.-L.; Wei, K.-H. *J. Phys. Chem. C* 2015, 119, 3408-3417. (d) Jung, J. W.; Russell, T. P.; Jo, W. H. *ACS Appl. Mater. Interfaces* 2015, 7, 13666-13674.

[9] (a) Liu, Y.; Zhao, J.; Li, Z.; Mu, C.; Ma, W.; Hu, H.; Jiang, K.; Lin, H.; Ade, H.; Yan, H. *Nat. Commun.* 2014, 5, 5293, 1-7. (b) Wu, Z.; Sun, C.; Dong, S.; Jiang, X.-F.; Wu, S.; Wu, H.; Yip, H.-L.; Huang, F.; Cao, Y. *J. Am. Chem. Soc.* 2016, 138, 2004-2013.

[10] For examples, see: (a) Leclerc, N.; Michaud, A.; Sirois, K.; Morin, J.-F.; Leclerc, M. *Adv. Funct. Mater.* 2006, 16, 1694-1704. (b) Bhuwalka, A.; Mike, J. F.; Intemann, J. J.; Ellern, A.; Jeffries-El, M. *Org. Biomol. Chem.* 2015, 13, 9462-9470.

[11] For examples, see: (a) Zrig, S.; Koeckelberghs, G.; Verbiest, T.; Andrioletti, B.; Rose, E.; Persoons, A.; Asselberghs, I.; Clays, K. *J. Org. Chem.* 2007, 72, 5855-5858.

[12] For examples, see: (a) Brzeczek, A.; Piwowar, K.; Domagala, W.; Mikolajczyk, M. M.; Walczak, K.; Wagner, P. *RSC Adv.* 2016, 6, 36500-36509.

[13] (a) Qi, T.; Guo, Y.; Liu, Y.; Xi, H.; Zhang, H.; Gao, X.; Liu, Y.; Lu, K.; Du, C.; Yu, G.; Zhu, D. *Chem. Commun.* 2008, 6227-6229. (b) Dienes, Y.; Eggenstein, M.; Kárpáti, T.; Sutherland, T. C.; Nyulászi, L.; Baumgartner, T. *Chem.-Eur. J.* 2008, 14, 9878-9889. (c) Oechsle, P.; Paradies, *J. Org. Lett.* 2014, 16, 4086-4089.

[14] (a) Al-Hashimi, M.; Labram, J. G.; Watkins, S.; Motevalli, M.; Anthopoulos, T. D.; Heeney, M. *Org. Lett.* 2010, 12, 5478-5481. (b) Mishra, A. K.; Vaidyanathan, S.; Noguchi, H.; Doetz, F.; Zhu, B.; Basuki, J. S. Chinese Patent CN103052643 (A), 2013.

[15] Li, H.; Fu, K.; Boix, P. P.; Wong, L. H.; Hagfeldt, A.; Gratzel, M.; Mhaisalkar, S. G.; Grimsdale, A. C. *ChemSusChem* 2014, 7, 3420-3425.

[16] For an example of this reductive homocoupling, see: Arroyave, F. A.; Richard, C. A.; Reynolds, J. R. *Org. Lett.* 2012, 14, 6138-6141.

[17] The 2,2'-bithiophene intermediate is commercially available, so in practice, usually only the bromination of 2,2'-bithiophene must be done by researchers. Alternatively, 5,5'-dibromo-2,2'-bithiophene can be purchased, although it is not cheap. For some examples of bromination references, see: (a) Dahlmann, U.; Neidlein, R. *Helv. Chim. Acta* 1996, 79, 755-766. (b) Colella, S.; Mazzeo, M.; Grisorio, R.; Fabiano, E.; Melcarne, G.; Carallo, S.; Angione, M. D.; Torsi, L.; Suranna, G. P.; della Sala, F.; Mastrorilli, P.; Gigli, G. *Chem. Commun.* 2010, 46, 6273-6275. (c) Getmanenko, Y. A.; Twieg, R. J. *J. Org. Chem.* 2008, 73, 830-839.

[18] Krasovskiy, A.; Tishkov, A.; del Amo, V.; Mayr, H.; Knochel, P. *Angew. Chem., Int. Ed.* 2006, 45, 5010-5014.

[19] For examples of this synthetic route, see ref 7a and the following: (a) Li, J.-C.; Lee, S.-H.; Hahn, Y.-B.; Kim, K.-J.; Zong, K.; Lee, Y.-S. *Synth. Metals* 2008, 158, 150-156. (b) Grenier, F.; Goudreau, K.; Leclerc, M. *J. Am. Chem. Soc.* 2017, 139, 2816-2824.

[20] See ref 6 for a discussion of the Pd-catalyzed stoichiometric Ag oxidative homocoupling synthesis of 2,2'-bithiophenes along with other synthetic methods.

[21] Masui, K.; Ikegami, H.; Mori, A. *J. Am. Chem. Soc.* 2004, 126, 5074-5075.

[22] (a) Kobayashi, K.; Sugie, A.; Takahashi, M.; Masui, K.; Mori, A. *Org. Lett.* 2005, 7, 5083-5085. (b) Takahashi, M.; Masui, K.; Sekiguchi, H.; Kobayashi, N.; Mori, A.; Funahashi, M.; Tamaoki, N. *J. Am. Chem. Soc.* 2006, 128, 10930-10933.

[23] Brouwer, F.; Alma, J.; Valkenier, H.; Voortman, T. P.; Hillebrand, J.; Chiechi, R. C.; Hummelen, J. C. *J. Mater. Chem.* 2011, 21, 1582-1592.

[24] Hassan, J.; Lavenot, L.; Gozzi, C.; Lemaire, M. *Tetrahedron Lett.* 1999, 40, 857-858.

[25] For an example, see: Durso, M.; Gentili, D.; Bettini, C.; Zanelli, A.; Cavallini, M.; De Angelis, F.; Lobello, M. G.; Biondo, V.; Muccini, M.; Capelli, R.; Melucci, M. *Chem. Commun.* 2013, 49, 4298-4300.

[26] Zhang, M.; Fan, H.; Guo, X.; Yang, Y.; Wang, S.; Zhang, Z.-G.; Zhang, J.; Zhan, X.; Li, Y. *J. Polym. Sci. Part A: Polym. Chem.* 2011, 49, 2746-2754.

[27] For papers that use 5,5'-dibromo-4,4'-dialkyl-2,2'-bithiophenes and the 5,5'-bis(trialkylstannyl)-4,4'-dialkyl-2,2'-bithiophene derivatives in the synthesis of organic materials, see: (a) Higuchi, H.; Yoshida, S.; Uraki, Y.; Ojima, J. *Bull. Chem. Soc. Jpn.* 1998, 71, 2229-2237. (b) Higuchi, H.; Ishikura, T.; Miyabayashi, K.; Miyake, M.; Yamamoto, K. *Tetrahedron Lett.* 1999, 40, 9091-9095. (c) Higuchi, H.; Ishikura, T.; Mori, K.; Takayama, Y.; Yamamoto, K.; Tani, K.; Miyabayashi, K.; Miyake, M. *Bull. Chem. Soc. Jpn.* 2001, 74, 889-906. (d) Hayashi, N.; Murayama, M.; Mori, K.; Matsuda, A.; Chikamatsu, E.; Tani, K.; Miyabayashi, K.; Miyake, M.; Higuchi, H. *Tetrahedron* 2004, 60, 6363-6383. (e) Hayashi, N.; Nishihara, T.; Matsukihira, T.; Nakashima, H.; Miyabayashi, K.; Miyake, M.; Higuchi, H. *Bull. Chem. Soc. Jpn.* 2007, 80, 371-386. (f) Aso, Y.; Ie, Y.; Okabe, M.; Nitani, M.; Ueda, M. European Patent 2,223,918 A1, 2010. (g) Zhang, J.; Deng, D.; He, C.; He, Y.; Zhang, M.; Zhang, Z.-G.; Zhang, Z.; Li, Y. *Chem. Mater.* 2011, 23, 817-822. (h) Amir, E.; Sivanandan, K.; Cochran, J. E.; Cowart, J. J.; Ku, S.-Y.; Seo, J. H.; Chabinyc, M. L.; Hawker, C. J. *J. Polym. Sci. Part A: Polym. Chem.* 2011, 49, 1933-1941. (i) Smeets, A.; Willot, P.; De Winter, J.; Gerbaux, P.; Verbiest, T.; Koeckelberghs, G. *Macromolecules* 2011, 44, 6017-6025. (j) Verswyvel, M.; Monnaie, F.; Koeckelberghs, G. *Macromolecules* 2011, 44, 9489-9498. (k) Ie, Y.; Okabe, M.; Aso, Y.; Ueda, M. European Patent 2,407, 465 A1, 2012. (1) Potash, S.; Rozen, S. *Chem.-Eur. 1* 2013, 19, 5289-5296. (m) Fernando, R.; Mao, Z.; Sauvé, G. *Org. Electron.* 2013, 14, 1683-1692. (n) Jeong, H.-G.; Khim, D.; Jung, E.; Yun, J.-M.; Kim, J.; Ku, J.; Jang, Y. H.; Kim, D.-Y. *J. Polym. Sci. Part A: Polym. Chem.* 2013, 51, 1029-1039. (o) Capozzi, B.; Dell, E. J.; Berkelbach, T. C.; Reichman, D. R.; Venkataraman, L.; Campos, L. M. *J. Am. Chem. Soc.* 2014, 136, 10486-10492. (p) Tang, A.; Zhan, C.; Yao, J. *Chem. Mater.* 2015, 27, 4719-4730. (q) Kim, H. G.; Kim, M.; Clement, J. A.; Lee, J.; Shin, J.; Hwang, H.; Sin, D. H.; Cho, K. *Chem. Mater.* 2015, 27, 6858-6868. (r) Zhang, X.; Yao, J.; Zhan, C. *Sci. China Chem.* 2016, 59, 209-217. (s) Li, H.; DeCoster, M. E.;

Ireland, R. M.; Song, J.; Hopkins, P. E.; Katz, H. E. *J. Am. Chem. Soc.* 2017, 139, 11149-11157.

[28] For some examples of uses of 5,5'-dibromo-2,2'-bithiophene specifically, see: (a) Han, W.-S.; Wee, K.-R.; Kim, H.-Y.; Pac, C.; Nabetani, Y.; Yamamoto, D.; Shimada, T.; Inoue, H.; Choi, H.; Cho, K.; Kang, S. O. *Chem.-Eur. J.* 2012, 18, 15368-15381. (b) Tao, T.; Ma, B.-B.; Peng, Y.-X.; Wang, X.-X.; Huang, W.; You, X.-Z. *J. Org. Chem.* 2013, 78, 8669-8679.

[29] A method for first row transition metal-catalyzed aerobic homocoupling of 2-chlorothiophene to give 5,5'-dichloro-2,2'-bithiophene and benzo[b]thiophene to give 2,2'-bibenzo[b]thiophene has been reported, but it relies on exotic bases prepared under anaerobic conditions from Grignard reagents with dry solvents and anhydrous metal salts and so has many of the same drawbacks that traditional homocoupling methods which rely on strong bases possess: (a) Do, H.-Q.; Daugulis, O. *J. Am. Chem. Soc.* 2009, 131, 17052-17053. (b) Truong, T.; Alvarado, J.; Tran, L. D.; Daugulis, O. *Org. Lett.* 2010, 12, 1200-1203.

[30] (a) Izawa, Y.; Stahl, S. S. *Adv. Synth. Catal.* 2010, 352, 3223-3229. (b) Campbell, A. N.; Meyer, E. B.; Stahl, S. S. *Chem. Commun.* 2011, 47, 10257-10259. (c) Li, N.-N.; Zhang, Y.-L.; Mao, S.; Gao, Y.-R.; Guo, D.-D.; Wang, Y.-Q. *Org. Lett.* 2014, 16, 2732-2735. (d) Wang, D.; Salazar, C.; Stahl, S. S. *Manuscript in preparation.*

[32] (a) Shiotani, A.; Yoshikiyo, M.; Itatani, H. *J. Mol. Catal.* 1983, 18, 23-31. (b) Shiotani, A.; Itatani, H.; Inagaki, T. *J. Mol. Catal.* 1986, 34, 57-66.

[33] We are aware of one Pd-catalyzed oxidative methodology with phd as a ligand that uses the stoichiometric oxidant N-fluorobenzenesulfonimide (NFSI): Yuan, Z.; Peng, H.; Liu, G. *Chin. J. Chem.* 2013, 31, 908-914.

We claim:

1. A catalytic system for catalyzing the synthesis of a 2,2'-bithiophene from two thiophenes, comprising:
   oxygen gas;
   palladium;
   a transition metal, alkali metal, alkaline earth metal, bismuth salt, or aluminum salt; and
   a ligand, wherein the ligand is selected from the group consisting of a 1,10-phenanthroline-5,6-dione, a 2,2'-bipyridine, a 2,2'-bipyrimidine, a 4,5-diazafluoren-9-one, a quinoline, a 1,10-phenanthroline, a bis(arylimino)acenaphthene, and a 2,2'-biquinoline.

2. The catalytic system of claim 1, wherein the ligand is a 1,10-phenanthroline-5,6-dione having the chemical formula:

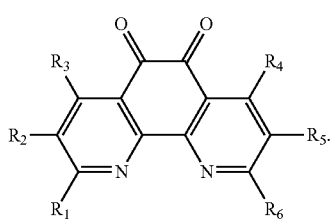

3. The catalytic system of claim 2, wherein 1, 2, 3, 4, or 5 of $R_1$, $R_2$, $R_3$, $R_4$, $R_5$ and $R_6$ are hydrogen, or wherein all 6 or $R_1$, $R_2$, $R_3$, $R_4$, $R_5$ and $R_6$ are hydrogen (the ligand is 1, 10-phenanthroline-5, 6-dione (phd)).

4. The catalytic system of claim 1, wherein the ligand is a 2,2'-bipyridine having the chemical formula:

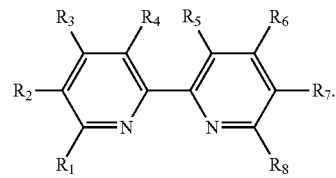

5. The catalytic system of claim 4, wherein one or more of $R_1$, $R_2$, $R_3$, $R_4$, $R_5$, $R_6$, $R_7$ and $R_8$ are independently selected from the group consisting of hydrogen, tert-butyl, methoxy, methyl, phenyl, and trifluoromethyl.

6. The catalytic system of claim 1, wherein the ligand is a 2,2'-bipyrimidine having the chemical formula:

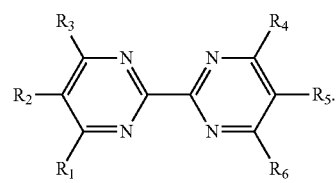

7. The catalytic system of claim 6, wherein one or more of $R_1$, $R_2$, $R_3$, $R_4$, $R_5$, and $R_6$ is hydrogen.

8. The catalytic system of claim 1, wherein the ligand is a 4,5-diazafluoren-9-one having the chemical formula:

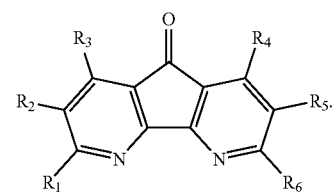

9. The catalytic system of claim 8, wherein one or more of $R_1$, $R_2$, $R_3$, $R_4$, $R_5$, and $R_6$ is hydrogen.

10. The catalytic system of claim 1, wherein the ligand is a quinoline having the chemical formula:

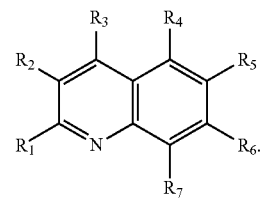

11. The catalytic system of claim 10, wherein one or more of $R_1$, $R_2$, $R_3$, $R_4$, $R_5$, $R_6$ and $R_7$ is hydrogen.

12. The catalytic system of claim 1, wherein the ligand is a 1,10-phenanthroline having the chemical formula:

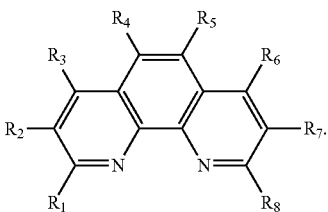

13. The catalytic system of claim 12, wherein one or more of $R_1$, $R_2$, $R_3$, $R_4$, $R_5$, $R_6$ $R_7$, and $R_8$ is independently selected from the group consisting of hydrogen, methyl, and phenyl.

14. The catalytic system of claim 1, wherein the ligand is a bis(arylimino)acenaphthene having the chemical formula:

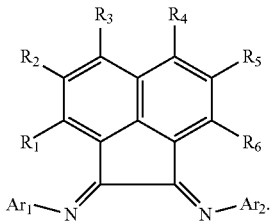

15. The catalytic system of claim 14, wherein one or more of $R_1$, $R_2$, $R_3$, $R_4$, $R_5$, and $R_6$ is hydrogen, or wherein one or both of $Ar_1$ and $Ar_2$ are selected from the group consisting of 4-methylphenyl and 1, 3, 4-trimethylphenyl.

16. The catalytic system of claim 1, wherein the ligand is a 2,2'-biquinoline having the chemical formula:

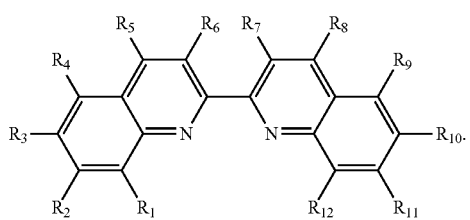

17. The catalytic system of claim 16, wherein one or more of $R_1$, $R_2$, $R_3$, $R_4$, $R_5$, $R_6$, $R_7$, $R_8$, $R_9$, $R_{10}$, $R_{11}$ and $R_{12}$ is hydrogen.

* * * * *

UNITED STATES PATENT AND TRADEMARK OFFICE
CERTIFICATE OF CORRECTION

Page 1 of 2

PATENT NO. : 11,773,074 B2
APPLICATION NO. : 17/087926
DATED : October 3, 2023
INVENTOR(S) : Shannon Stahl et al.

It is certified that error appears in the above-identified patent and that said Letters Patent is hereby corrected as shown below:

In the Specification

Column 2, Line 31, "20D" should be --2OD--.

Column 3, Line 10, "(Cl$_2$H$_{25}$)" should be --"(C$_{12}$H$_{25}$)--.

Column 12, Line 63, " 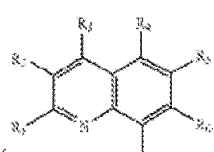 " should be -- 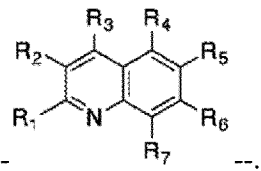 --.

Column 18, Line 20, "[Pd(OAc)$_2$/Cu(OAc)$_2$•4H$_2$O]" should be --[Pd(OAc)$_2$/Mn(OAc)$_2$•4H$_2$O]--.

Column 29, Entry 4, " 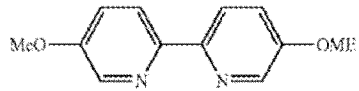 " should be --  --.

Column 31, Entry 9, "4,7-diphenyl-2,9-dimethyl-1,10-phenanthroline" should be --4,7-diphenyl-1,10-phenanthroline--.

Column 39, Line Table 5, Entry 3, "'BuBQ" should be --$^t$BuBQ--.

Column 46, Line 49, "CO" should be --Cu$^{II}$--.

Column 48, Line 60, "h$_H$/k$_D$" should be --k$_H$/k$_D$--.

Column 48, Line 62, "h$_H$/k$_D$" should be --k$_H$/k$_D$--.

Signed and Sealed this
Twenty-seventh Day of August, 2024

Katherine Kelly Vidal
*Director of the United States Patent and Trademark Office*

Column 48, Line 64, "ME" should be --KIE--.

Column 52, Line 55, "Eur. 1" should be --Eur. J.--.